(12) United States Patent
Quigley

(10) Patent No.: US 10,293,135 B2
(45) Date of Patent: May 21, 2019

(54) DELIVERY CATHETER FOR AND METHOD OF DELIVERING IMPLANT, FOR EXAMPLE, BRONCHOSCOPICALLY IMPLANTING A MARKER IN A LUNG

(71) Applicant: Varian Medical Systems, Inc., Palo Alto, CA (US)

(72) Inventor: Fergus Quigley, Seattle, WA (US)

(73) Assignee: VARIAN MEDICAL SYSTEMS, INC., Palo Alto, CA (US)

( * ) Notice: Subject to any disclaimer, the term of this patent is extended or adjusted under 35 U.S.C. 154(b) by 158 days.

(21) Appl. No.: 15/385,121

(22) Filed: Dec. 20, 2016

(65) Prior Publication Data

US 2017/0209666 A1     Jul. 27, 2017

Related U.S. Application Data

(62) Division of application No. 13/877,257, filed as application No. PCT/US2011/054656 on Oct. 3, 2011, now Pat. No. 9,545,506.

(Continued)

(51) Int. Cl.
    *A61B 1/00*           (2006.01)
    *A61M 25/00*        (2006.01)
(Continued)

(52) U.S. Cl.
    CPC .............. *A61M 25/00* (2013.01); *A61B 90/39* (2016.02); *A61M 25/0105* (2013.01);
(Continued)

(58) Field of Classification Search
    CPC .............. A61M 25/00; A61M 25/0108; A61M 25/0105; A61M 25/09; A61M 2025/09166; A61B 1/2676; A61B 1/267
See application file for complete search history.

(56) References Cited

U.S. PATENT DOCUMENTS 3,967,161 A    6/1976   Lichtblau
4,023,167 A    5/1977   Wahlstrom
(Continued)

FOREIGN PATENT DOCUMENTS

JP           07313515       12/1995
JP          2001008947      1/2001
(Continued)

OTHER PUBLICATIONS

Beyer, Thomas et al., "Dual-modality PET/CT Imaging: the effect of respiratory motion on combined image quality in clinical oncology," European Journal of Nuclear Medicine and Molecular Imagining 30.4 (2003): pp. 588-596.

(Continued)

*Primary Examiner* — Timothy J Neal
(74) *Attorney, Agent, or Firm* — Perkins Coie LLP

(57) ABSTRACT

Systems and methods for treating a lung of a lung of a patient. One embodiment of a method comprises positioning a leadless marker in the lung of the patient relative to the target, and collecting position data of the marker. This method further comprises determining the location of the marker in an external reference frame outside the patient based on the collected position data, and providing an objective output in the external reference frame that is responsive to movement of the marker. The objective output is provided at a frequency (i.e., periodicity) that results in a clinically acceptable tracking error. In addition, the objective output can also be provided at least substantially contemporaneously with collecting the position data used to determine the location of the marker.

20 Claims, 27 Drawing Sheets

Related U.S. Application Data

(60) Provisional application No. 61/389,184, filed on Oct. 1, 2010.

(51) Int. Cl.

| | | |
|---|---|---|
| *A61M 31/00* | (2006.01) | |
| *A61N 5/10* | (2006.01) | |
| *A61B 90/00* | (2016.01) | |
| *A61M 25/01* | (2006.01) | |
| *A61M 25/09* | (2006.01) | |
| A61B 17/00 | (2006.01) | |
| A61B 34/20 | (2016.01) | |
| A61B 1/267 | (2006.01) | |

(52) U.S. Cl.
CPC ........ *A61M 25/0108* (2013.01); *A61M 25/09* (2013.01); *A61M 31/005* (2013.01); *A61N 5/1049* (2013.01); *A61B 1/2676* (2013.01); *A61B 2017/00867* (2013.01); *A61B 2034/2051* (2016.02); *A61B 2090/3987* (2016.02); *A61B 2090/3991* (2016.02); *A61M 2025/09166* (2013.01)

(56) References Cited

U.S. PATENT DOCUMENTS

| | | |
|---|---|---|
| 4,114,601 A | 9/1978 | Abels |
| 4,123,749 A | 10/1978 | Hartmann et al. |
| 4,127,110 A | 11/1978 | Bullara |
| 4,160,971 A | 7/1979 | Jones et al. |
| 4,216,860 A | 8/1980 | Heimann |
| 4,222,374 A | 9/1980 | Sampson et al. |
| 4,260,990 A | 4/1981 | Lichtblau |
| 4,393,872 A | 7/1983 | Reznik et al. |
| 4,618,822 A | 10/1986 | Hansen |
| 4,633,250 A | 12/1986 | Anderson |
| 4,643,196 A | 2/1987 | Tanaka et al. |
| 4,696,287 A | 9/1987 | Hortmann et al. |
| 4,795,995 A | 1/1989 | Eccleston et al. |
| 4,799,495 A | 1/1989 | Hawkins et al. |
| 4,900,303 A | 2/1990 | Lemelson |
| 4,909,789 A | 3/1990 | Taguchi |
| 4,936,823 A | 6/1990 | Colvin et al. |
| 4,945,914 A | 8/1990 | Allen |
| 4,994,079 A | 2/1991 | Genese et al. |
| 5,031,634 A | 7/1991 | Simon |
| 5,095,224 A | 3/1992 | Renger |
| 5,099,845 A | 3/1992 | Besz |
| 5,107,862 A | 4/1992 | Fabian |
| 5,142,292 A | 8/1992 | Chang |
| 5,152,776 A | 10/1992 | Pinchuk |
| 5,170,055 A | 12/1992 | Carroll |
| 5,325,873 A | 7/1994 | Hirschi et al. |
| 5,353,804 A | 10/1994 | Kornberg |
| 5,395,332 A * | 3/1995 | Ressemann ....... A61M 25/0068 600/585 |
| 5,409,004 A | 4/1995 | Sloan |
| 5,423,334 A | 6/1995 | Jordan |
| 5,425,367 A | 6/1995 | Shapiro et al. |
| 5,425,382 A | 6/1995 | Golden et al. |
| 5,446,548 A | 8/1995 | Gerig et al. |
| 5,509,900 A | 4/1996 | Kirkman |
| 5,528,651 A | 6/1996 | Leksell et al. |
| 5,626,630 A | 5/1997 | Markowitz et al. |
| 5,638,819 A | 6/1997 | Manwaring |
| 5,651,043 A | 7/1997 | Tsuyuki et al. |
| 5,680,106 A | 10/1997 | Schrott et al. |
| 5,707,362 A | 1/1998 | Yoon |
| 5,707,390 A | 1/1998 | Bonutti |
| 5,711,299 A | 1/1998 | Manwaring |
| 5,727,552 A | 3/1998 | Ryan |
| 5,735,795 A | 4/1998 | Young |
| 5,748,767 A | 5/1998 | Raab |
| 5,754,623 A | 5/1998 | Seki |
| 5,757,881 A | 5/1998 | Hughes |
| 5,764,052 A | 6/1998 | Renger |
| 5,769,861 A | 6/1998 | Vilsmeier |
| 5,810,851 A | 9/1998 | Yoon |
| 5,815,076 A | 9/1998 | Herring |
| 5,840,148 A | 11/1998 | Campbell et al. |
| 5,868,673 A | 2/1999 | Vesely |
| 5,879,297 A | 3/1999 | Somogyi |
| 5,879,357 A | 3/1999 | Heaton et al. |
| 5,910,144 A | 6/1999 | Hayashi |
| 5,928,137 A | 7/1999 | Green |
| 5,951,481 A | 9/1999 | Evans |
| 5,957,934 A | 9/1999 | Rapoport |
| 5,989,265 A | 11/1999 | Bouquet De La Joliniere |
| 6,026,818 A | 2/2000 | Blair et al. |
| 6,059,734 A | 5/2000 | Yoon |
| 6,061,644 A | 5/2000 | Leis |
| 6,067,465 A | 5/2000 | Foo et al. |
| 6,076,008 A | 6/2000 | Bucholz |
| 6,081,238 A | 6/2000 | Alicot |
| 6,082,366 A | 7/2000 | Andra |
| 6,144,875 A | 11/2000 | Schweikard et al. |
| 6,161,009 A | 12/2000 | Wheless, Jr. |
| 6,198,963 B1 | 3/2001 | Haim et al. |
| 6,246,900 B1 | 6/2001 | Cundari |
| 6,264,599 B1 * | 7/2001 | Slater ................... A61N 5/1027 600/7 |
| 6,307,473 B1 | 10/2001 | Zampini |
| 6,325,758 B1 | 12/2001 | Carol et al. |
| 6,353,655 B1 | 3/2002 | Siochi |
| 6,359,959 B1 | 3/2002 | Chapman |
| 6,363,940 B1 | 4/2002 | Krag |
| 6,371,379 B1 | 4/2002 | Dames et al. |
| 6,377,162 B1 | 4/2002 | Delestienne |
| 6,381,485 B1 | 4/2002 | Hunter et al. |
| 6,385,286 B1 | 5/2002 | Fitchard et al. |
| 6,385,288 B1 | 5/2002 | Kanematsu |
| 6,393,096 B1 | 5/2002 | Carol et al. |
| 6,405,072 B1 | 6/2002 | Cosman |
| 6,416,520 B1 | 7/2002 | Kynast et al. |
| 6,501,981 B1 | 12/2002 | Schweikard et al. |
| 6,510,199 B1 | 1/2003 | Falkenstein |
| 6,535,756 B1 | 3/2003 | Simon et al. |
| 6,650,930 B2 | 11/2003 | Ding |
| 6,662,036 B2 | 12/2003 | Cosman |
| 6,675,810 B2 | 1/2004 | Krag |
| 6,698,433 B2 | 3/2004 | Krag |
| 6,702,780 B1 | 3/2004 | Gilboa et al. |
| 6,812,842 B2 | 11/2004 | Dimmer |
| 6,822,570 B2 | 11/2004 | Dimmer |
| 6,838,990 B2 | 1/2005 | Dimmer |
| 6,882,947 B2 | 4/2005 | Levin |
| 6,918,919 B2 | 7/2005 | Krag |
| 6,934,356 B1 | 8/2005 | Satheesan et al. |
| 6,937,696 B1 | 8/2005 | Mostafavi |
| 6,961,405 B2 | 11/2005 | Scherch |
| 6,977,504 B2 | 12/2005 | Wright et al. |
| 6,993,112 B2 | 1/2006 | Hesse |
| 6,994,712 B1 | 2/2006 | Fisher et al. |
| 6,999,555 B2 | 2/2006 | Morf |
| 7,026,927 B2 | 4/2006 | Wright |
| 7,027,707 B2 | 4/2006 | Imaki |
| 7,077,842 B1 | 7/2006 | Cosman |
| 7,142,905 B2 | 11/2006 | Slayton |
| 7,154,991 B2 | 12/2006 | Earnst |
| 7,206,626 B2 | 4/2007 | Quaid |
| 7,206,627 B2 | 4/2007 | Quaid, III |
| 7,213,009 B2 | 5/2007 | Pestotnik |
| 7,221,733 B1 | 5/2007 | Takai |
| 7,247,160 B2 | 7/2007 | Seiler |
| 7,280,863 B2 | 10/2007 | Shacher |
| 7,289,839 B2 | 10/2007 | Dimmer |
| 7,318,805 B2 | 1/2008 | Schweikard |
| 7,447,643 B1 | 11/2008 | Olson |
| 7,606,405 B2 | 10/2009 | Sawyer |
| 8,079,964 B2 | 12/2011 | Reichel et al. |
| 8,239,005 B2 | 8/2012 | Wright et al. |
| 9,283,053 B2 | 3/2016 | Dimmer |
| 2001/0029509 A1 | 10/2001 | Schaewe |

(56) References Cited

U.S. PATENT DOCUMENTS

| | | |
|---|---|---|
| 2002/0049362 A1 | 4/2002 | Ding |
| 2002/0065455 A1 | 5/2002 | Ben-Haim et al. |
| 2002/0065461 A1 | 5/2002 | Cosman |
| 2002/0165443 A1 | 11/2002 | Mori |
| 2002/0193685 A1 | 12/2002 | Mate et al. |
| 2003/0002621 A1 | 1/2003 | Falkenstein |
| 2003/0023161 A1 | 1/2003 | Schwartz |
| 2003/0052785 A1 | 3/2003 | Gisselberg et al. |
| 2003/0070682 A1 | 4/2003 | Wilson et al. |
| 2003/0125622 A1 | 7/2003 | Schweikard et al. |
| 2003/0153829 A1 | 8/2003 | Pratt |
| 2003/0192557 A1 | 10/2003 | Moody |
| 2003/0206610 A1 | 11/2003 | Collins |
| 2003/0206614 A1 | 11/2003 | Meeks |
| 2003/0212412 A1 | 11/2003 | Dillard et al. |
| 2004/0019274 A1 | 1/2004 | Herline |
| 2004/0068182 A1 | 4/2004 | Misra |
| 2004/0096033 A1 | 5/2004 | Seppi |
| 2004/0116804 A1 | 6/2004 | Mostafavi |
| 2004/0122308 A1 | 6/2004 | Ding |
| 2004/0122311 A1 | 6/2004 | Cosman |
| 2004/0123871 A1 | 7/2004 | Wright et al. |
| 2004/0124105 A1 | 7/2004 | Seiler et al. |
| 2004/0125916 A1 | 7/2004 | White |
| 2004/0127787 A1 | 7/2004 | Hadford |
| 2004/0133101 A1 | 7/2004 | Dimmer |
| 2004/0138555 A1 | 7/2004 | Moody |
| 2004/0162574 A1 | 8/2004 | Viola |
| 2004/0176931 A1 | 9/2004 | Friemel |
| 2005/0059884 A1 | 3/2005 | Krag |
| 2005/0059887 A1 | 3/2005 | Sloutsky |
| 2005/0077459 A1 | 4/2005 | Engler |
| 2005/0151649 A1 | 7/2005 | Wright |
| 2005/0154280 A1 | 7/2005 | Wright |
| 2005/0154284 A1 | 7/2005 | Wright |
| 2005/0154293 A1 | 7/2005 | Gisselberg et al. |
| 2005/0251111 A1 | 11/2005 | Saito et al. |
| 2005/0261570 A1 | 11/2005 | Dimmer |
| 2006/0015171 A1* | 1/2006 | Armstrong ....... A61B 17/12022 623/1.12 |
| 2006/0052694 A1 | 3/2006 | Phillips |
| 2006/0058548 A1 | 3/2006 | Kim |
| 2006/0063999 A1 | 3/2006 | Rolfes |
| 2006/0074301 A1 | 4/2006 | Wright |
| 2006/0074302 A1 | 4/2006 | Wright |
| 2006/0078086 A1 | 4/2006 | Wright |
| 2006/0079764 A1 | 4/2006 | Wright et al. |
| 2006/0093089 A1 | 5/2006 | Vertatschitsch et al. |
| 2006/0100509 A1 | 5/2006 | Dimmer |
| 2007/0106108 A1 | 5/2007 | Hermann et al. |
| 2007/0161884 A1 | 7/2007 | Widener |
| 2008/0226149 A1 | 9/2008 | Meyer |
| 2010/0036241 A1 | 2/2010 | Mayse et al. |
| 2010/0042041 A1* | 2/2010 | Tune ................. A61M 37/0069 604/60 |
| 2012/0101331 A1 | 4/2012 | Gilad et al. |

FOREIGN PATENT DOCUMENTS

| | | | |
|---|---|---|---|
| JP | 2004154548 | 6/2004 | |
| WO | 9608208 | 3/1996 | |
| WO | WO 9712553 | 4/1997 | |
| WO | WO 9830166 | 7/1998 | |
| WO | WO 9840026 | 9/1998 | |
| WO | WO 9838908 | 11/1998 | |
| WO | WO 9927839 | 6/1999 | |
| WO | WO 9930182 | 6/1999 | |
| WO | WO 9933406 | 7/1999 | |
| WO | WO 9940869 | 8/1999 | |
| WO | WO 9958044 | 11/1999 | |
| WO | WO 9958065 | 11/1999 | |
| WO | 0038579 | 7/2000 | |
| WO | 0051514 | 9/2000 | |
| WO | WO 0065989 | 11/2000 | |
| WO | WO 0239917 | 5/2002 | |
| WO | WO 0239918 | 5/2002 | |
| WO | WO 03053270 | 7/2002 | |
| WO | 03053270 | 7/2003 | |
| WO | 2005067563 | 7/2005 | |
| WO | WO 2005067563 | 7/2005 | |
| WO | WO-2007035798 A2 * | 3/2007 | ............ A61M 25/09 |

OTHER PUBLICATIONS

Low, Daniel A. et al., "A method for reconstruction of four-dimensional synchronized CT scans acquired during free breathing," Medical Physics 30.6 (2003), pp. 1254-1263.

Seiler, P. G. et al., "A Novel Tracking Technique for the Continuous Precise Measurement of Tumour Positions in Conformal Therapy," Jun. 7, 2000, IOP Publishing Ltd., Phys. Med. Biol., vol. 45, pp. N103-N110.

Seppenwoolde et al., "Precise and Real-Time Measurement of 3D Tumor Motion in Lung due to Breathing and Heartbeat, Measured During Radiotherapy," Int. J. Radiant. Oncol.. Biol. Phys. Jul. 15, 2002, 53, pp. 822-834.

Wolthaus, J. W. H. et al., "Fusion of Respiration-Correlated PET and CT Scans: Correlated Lung Tumour Motion in Anatomical and Functional Scans," Physics in Medicine and Biology 50.7 (2005); pp. 1569.

International Search Report and Written Opinion issued for PCT/US2011/054656 and dated Jan. 31, 2012.

Sharp, et al., "Prediction of Respiratory Tumour Motion for Real-Time Image-Guided Radiotherapy", Phys. Med. Jan. 16, 2004, 16 pp.

* cited by examiner

DELIVERY CATHETER FOR AND METHOD OF DELIVERING IMPLANT, FOR EXAMPLE, BRONCHOSCOPICALLY IMPLANTING A MARKER IN A LUNG

CROSS-REFERENCE TO RELATED APPLICATIONS

This application is a divisional of U.S. patent application Ser. No. 13/877,257, filed on Sep. 16, 2013, which is a 371 U.S. national phase application of PCT/US2011/054656, filed on Oct. 3, 2011, which claims the benefit of U.S. Provisional Patent Application No. 61/389,184, filed Oct. 1, 2010, all of which are incorporated herein by reference their entirety.

TECHNICAL FIELD

The present invention is directed toward bronchoscopically implanting markers in the lung of a patient and more particularly, toward a pre-loaded delivery catheter with a marker wherein the marker includes an improved anti-migration device.

BACKGROUND

Radiation therapy has become a significant and highly successful process for treating prostate cancer, lung cancer, brain cancer and many other types of localized cancers. Radiation therapy procedures generally involve (a) planning processes to determine the parameters of the radiation (e.g., dose, shape, etc.), (b) patient setup processes to position the target at a desired location relative to the radiation beam, (c) radiation sessions to irradiate the cancer, and (d) verification processes to assess the efficacy of the radiation sessions. Many radiation therapy procedures require several radiation sessions (i.e., radiation fractions) over a period of approximately 5-45 days.

To improve the treatment of localized cancers with radiotherapy, it is generally desirable to increase the radiation dose because higher doses are more effective at destroying most cancers. Increasing the radiation dose, however, also increases the potential for complications to healthy tissues. The efficacy of radiation therapy accordingly depends on both the total dose of radiation delivered to the tumor and the dose of radiation delivered to normal tissue adjacent to the tumor. To protect the normal tissue adjacent to the tumor, the radiation should be prescribed to a tight treatment margin around the target such that only a small volume of healthy tissue is irradiated. For example, the treatment margin for prostate cancer should be selected to avoid irradiating rectal, bladder and bulbar urethral tissues. Similarly, the treatment margin for lung cancer should be selected to avoid irradiating healthy lung tissue or other tissue. Therefore, it is not only desirable to increase the radiation dose delivered to the tumor, but it also desirable to mitigate irradiating healthy tissue.

One difficulty of radiation therapy is that the target often moves within the patient either during or between radiation sessions. For example, tumors in the lungs move during radiation sessions because of respiration motion and cardiac functions (e.g., heartbeats and vasculature constriction/expansion). To compensate for such movement, the treatment margins are generally larger than desired so that the tumor does not move out of the treatment volume. However, this is not a desirable solution because the larger treatment margins may irradiate a larger volume of normal tissue.

Localization and/or tracking of markers, such as gold fiducials or electromagnetic transponders, implanted in proximity to the target or tumor may enable increased tumor radiation and decreased healthy tissue irradiation. However, fluoroscopic imaging of implanted gold fiducials is limited by high doses of non-therapeutic imaging radiation, expensive fluoroscopic equipment, subjective image interpretation and poor implant stability.

Another challenge in radiation therapy is accurately aligning the tumor with the radiation beam. Current setup procedures generally align external reference markings on the patient with visual alignment guides for the radiation delivery device. For an example, a tumor is first identified within the patient using an imaging system (e.g., X-ray, computerized tomography (CT), magnetic resonance imaging (MRI), or ultrasound system). The approximate location of the tumor relative to two or more alignment points on the exterior of the patient is then determined. During setup, the external marks are aligned with a reference frame of the radiation delivery device to position the treatment target within the patient at the beam isocenter of the radiation beam (also referenced herein as the machine isocenter). Conventional setup procedures using external marks are generally inadequate because the target may move relative to the external marks between the patient planning procedure and the treatment session and/or during the treatment session. As such, the target may be offset from the machine isocenter even when the external marks are at their predetermined locations for positioning the target at the machine isocenter. Reducing or eliminating such an offset is desirable because any initial misalignment between the target and the radiation beam will likely cause normal tissue to be irradiated. Moreover, if the target moves during treatment because of respiration, organ filling, or cardiac conditions, any initial misalignment will likely further exacerbate irradiation of normal tissue. Thus, the day-by-day and moment-by-moment changes in target motion have posed significant challenges for increasing the radiation dose applied to patients.

Conventional setup and treatment procedures using external marks also require a direct line-of-sight between the marks and a detector. This requirement renders these systems useless for implanted markers or markers that are otherwise in the patient (i.e., out of the line-of-sight of the detector and/or the light source). Thus, conventional optical tracking systems have many restrictions that limit their utility in medical applications. Thus, there is a continuing need for improved localization and tracking of markers, including an improved method of placing the marker and an improved system of preventing movement of the marker once placed.

Tumor target localization has been demonstrated utilizing implanted markers such as gold fiducials (balls and cylinders) and electromagnetic transponders. One method of placement for these markers in the lung is to deliver them into the bronchus/bronchioles of the lung and then force-fit the markers into the appropriate diameter bronchiole near the treatment target location. The implant location that permits a force-fit of the markers is likely not the most desired location, but one that simply accommodates the force fit. Additionally, the act of breathing, which effects a small enlargement/contraction cycle of the bronchioles, may dislodge the marker from its desired location. Many inhaled drugs also effect changes in the diameter of the bronchioles. Further, actions such as coughing, which typically originate in the alveolar structures near the lung periphery, serve to force the markers from their desired locations to locations closer to the trachea.

Thus implanted marker usage for localization and tracking of lung tissue targets has proven challenging due to marker migration issues. Since markers are surrogates for the actual treatment target position, there is a need to minimize potential for marker migration throughout the entire course of radiation therapy (from treatment planning to last radiation fraction application). Initial positioning and maintenance of marker location should desirably be accomplished independent of bronchus/bronchiole size. The position of the marker needs to remain stationary regardless of feature changes within the bronchioles. A multiplicity of devices, methods, and systems are listed to accomplish that task.

The airways in the lungs anatomically constitute an extensive network of conduits that reach all lung areas and lung tissues. Air enters the airways through the nose or mouth, travels through the trachea and into the bronchi and bronchioli of the lunch. The lungs are covered by a think membrane called the pleura. Because of these physiological characteristics of the airways, a marker placed in bronchi and bronchioli may cause pneumothorax when implanted, thus, there is a need for a new and improved device, system, and method for implanting a marker in the region proximate to a tumor or other lesion in the lung.

One recent method for locating a target implanted within the body includes a wireless implantable marker configured to be implanted surgically or percutaneously into a human body relative to a target location. The markers include a casing and a signal element in the casing that wirelessly transmits location signals in response to an excitation energy. One concern of using implanted markers in soft tissues, bronchi or bronchioli is that the markers may move within the patient after implantation. To resolve this concern, Calypso Medical Technologies, Inc. previously developed several anchors and fasteners for securing the markers to soft tissue structures, as disclosed in U.S. application Ser. No. 10/438,550, which is incorporated herein by reference. Although these anchors may work for percutaneous or surgical implantation, they may be improved for bronchoscopic applications. Therefore, it would be desirable to further develop markers for bronchoscopic deployment and implantation.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1A:
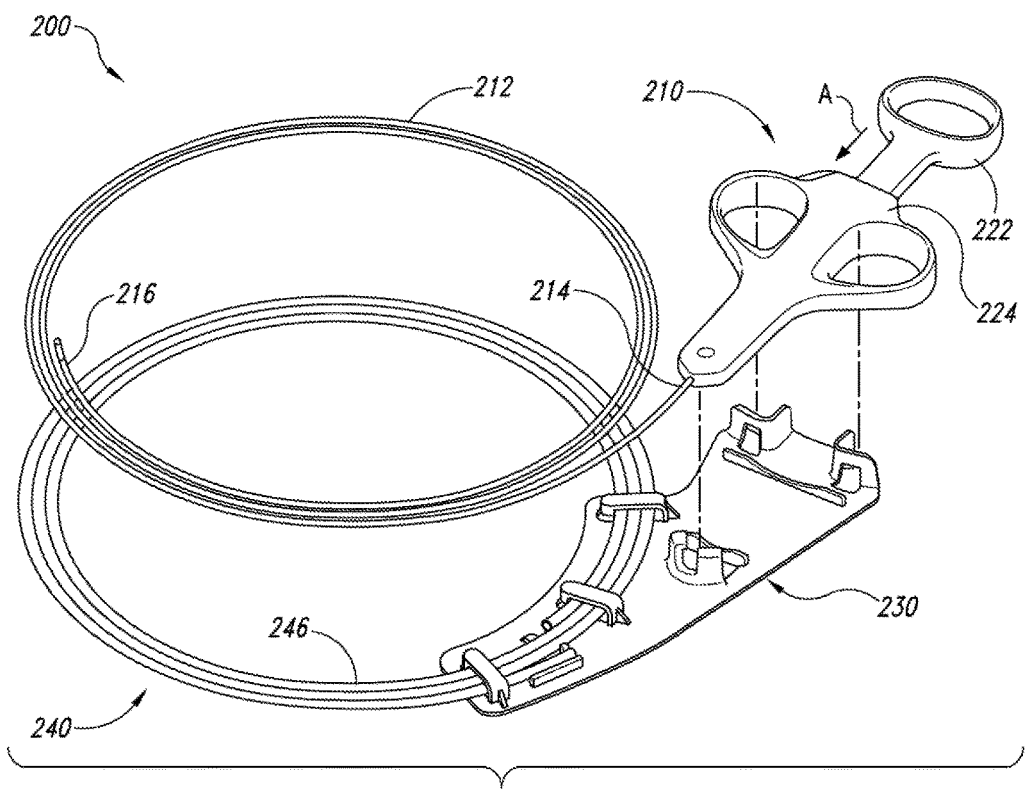
FIG. 1A is an isometric view of a bronchoscopic catheter assembly and a storage and transportation device configured in accordance with an embodiment of the present technology.

In the following description, certain specific details are set forth in order to provide a thorough understanding of various embodiments of the invention. However, one skilled in the relevant art will recognize that the invention may be practiced without one or more of these specific details, or with other methods, components, materials, etc. In other instances, well-known structures associated with the system, the bronchoscope catheter assembly, the marker, the anti-migration device and/or the storage device have not been shown or described in detail to avoid unnecessarily obscuring descriptions of the embodiments of the invention.

Several embodiments and features of a bronchoscopic catheter assembly, a marker or a marker with anchors in accordance with embodiments of the invention are set forth and described in the Figures. In other embodiments of the invention, the markers can include additional or different features than those shown in the Figures. Additionally, several embodiments of markers in accordance with the invention may not include all the features shown in these Figures. For the purposes of brevity, like reference numbers refer to similar or identical components of the markers in the Figures. Additionally, throughout the specification, claims, and drawings, the term "proximal" means nearest the trachea, and "distal" means nearest the alveoli.

The headings provided herein are for convenience only and do not interpret the scope or meaning of the claimed invention.

A. Overview

The following disclosure describes several embodiments of wireless markers configured to be implanted and anchored within the lung of a human in a manner that prevents the markers from migrating from the implantation site. The marker is configured to reduce pneumothorax and may further be configured to include an anchor or anti-migration device.

According to aspects of the invention, a bronchoscopic catheter assembly includes a marker pre-loaded at a distal end of a delivery catheter for bronchoscopically implanting the marker in peripheral airways of the lung. According to further aspects of the invention, a marker storage and loading device for retaining the marker prior to loading in the distal end of the delivery catheter is provided. The marker can extend a selected distance beyond the distal end of the delivery catheter to provide a leading end. According to aspects of the invention, the marker is configured at the leading end to reduce pneumothorax. According to further aspects of the invention, the marker includes an integral anti-migration or anchoring device for preventing migration of the marker after placement of the marker in the lung. According to still further aspects of the invention, an anti-migration device is separate from the marker and positioned adjacent to the deployed marker to prevent migration of the marker in the lung after placement. According to still further aspects of the invention, the marker is shaped and sized to reduce migration.

According to aspects of the invention, a marker for use in the bronchoscopic catheter assembly for localizing a target of a patient comprises a casing, a magnetic transponder at least partially received in the casing, and an anchor carried by the casing. The casing is a biocompatible barrier configured to be implanted in the patient. The casing can be a generally cylindrical capsule that is sized to fit within a catheter of a bronchoscope for bronchoscopic implantation, but the casing can have other geometric shapes, sizes, and configurations in other applications. For example, the casing can be larger for implanting the marker in the bronchus. The magnetic transponder produces a wirelessly transmitted magnetic field in response to a wirelessly transmitted excitation energy. The magnetic transponder can further comprise a magnetic core, a coil wrapped around the core, and a capacitor coupled to the coil. The anchor, which can project from the casing, be integral to the casing, or be independent from the casing, secures the marker to an anatomical structure once the marker has been deployed from the bronchoscopic catheter assembly to prevent the marker from moving from the implantation site. According to aspects, the anchor may be detached from the marker. In another embodiment, the marker may be secured to the anatomical structure by mechanical members or chemical attributes.

According to further aspects, an anchorable marker configured for bronchoscopic implantation for localizing a target of a patient comprises a casing, a transponder that produces a wirelessly transmitted magnetic field in response to a wirelessly transmitted excitation field, and an anchor partially embedded within the casing. The anchor can further be configured for bronchoscopic implantation and have a shape and/or material that pierces, engages or otherwise interfaces with the anatomical anchoring site such that the marker cannot be easily dislodged. Alternatively, the casing is shaped to reduce migration of the marker, for example, the casing may be wedge shaped, include a hook, or have a surface texture.

The invention further includes methods for manufacturing and using markers with anchors. One embodiment of such a method comprises providing a transponder that produces a wirelessly transmitted magnetic field in response to a wirelessly transmitted excitation field and forming a casing around the transponder. This method can further include embedding, attaching or forming an anchor in the casing. In alternative embodiments, the marker may be a gold fiducial, RFID tag, active marker or electromagnetic marker. In still further alternative embodiments, the anchor can be detached from the marker. In further embodiments, the casing may be the anchor.

According to one current practice, the marker is forcibly wedged into the lumen, however, this will work only for limited settings and circumstances. The marker must be approximately the same size as the lumen at the desired geographic placement location. The luminal wall must possess the appropriate elastic characteristics to retain the force-fitted marker. Forces such as those caused by coughing and wheezing serve to dislodge the marker. Potentially, mucous transport systems in the bronchioles could dislodge a force-fit marker. Inhaled drugs may serve as broncho-dilators and broncho-constrictors. Further, tumor shrinkage during radiation therapy and/or chemotherapy, diaphragmatic motion, the movement of air, and the various pressure profiles within the lung may serve to dislodge a positional marker.

Human lungs are located on either side of the heart and occupying a large portion of the chest cavity from the collarbone to the diaphragm. The lungs are covered by a thin membrane called the pleura. Air travels to the chest cavity through the trachea, which divides into two bronchi, each of which enters a lung. The bronchi divide and subdivide into a network of countless tubules. The smallest tubules, or bronchioles, enter cup-shaped air sacs known as alveoli, which number about 700 million in both lungs. In the case of a marker that is force-fit into a bronchiole, given that bronchioles decrease in diameter toward the lung periphery, any marker dislodgement would typically result in the marker moving toward the trachea, since there is no mechanism to force the marker further into the decreasing diameter lumen. So, in the case of a force fit marker, a solitary secondary plug could serve to secure the marker in place. Feasibly, since the marker should not move further down the bronchiole structure due to its decreasing luminal diameter, the secondary securing device would need to provide only a marginal increase in holding capacity to keep the marker in place. It should be noted that in this case, since the retention device is located on the side closer to the trachea side, it will be located in a diameter that is incrementally larger than that of the marker location.

Dependant upon the specific elastic properties at any specific bronchial location, a plurality of devices and methods exist for entrapping a marker in the bronchial lumen. A LRD (luminal retention device) embodied as a plug can be force fit into a tubular structure such as a bronchus, or other bodily lumen, to trap or hold in place a marker. A LRD rigid plug would rely on the resiliency of the lumen to hold the plug in place, while a plug constructed of silicone, sponge, or other similar materials would inherently possess its own resiliency. The fibrin-thrombin type adhesives and adhesive blobs could be used to a) build a LRD plug in-place in the lumen to prevent the marker from dislodging, b) augment the diameter or attach a smaller sized LRD plug to the luminal wall, or c) used to glue the transponder directly to the wall. Cyanoacrylate adhesives could be used in this application as well. A related product, the foamed-matrix biologically-based materials possess mechanical properties similar to weak plastics prior to being exposed to body fluids, and could be pre-formed into acceptable shapes to force-fit into a lumen, but would shortly form a soft, biologically based plug once established in the mucous of the bronchial tree.

Many shapes can be utilized as an LRD anchor or plug, since the goal is to fixate the marker. Materials many include plastics, metals, adhesives, expandable sponges, and bio-materials (e.g. collagen, connective tissue derivatives). Additional embodiments include: wire or shaped metal "ring", hex, umbrella, etc. A form resembling a helical shaped wire spring can be advanced through a small diameter conduit to the desired location in a compressed state, expanding to the luminal diameter upon expulsion from the confines of the conduit, trapping the marker on one side. A plurality of materials could be utilized, including, at least, metals, plastics, and matrix materials such as carbon-fiber.

Further, the internally-springed, radially self-expander marker anchor allows for diametral growth or shrinkage of the lumen in which it resides, without requiring adjustment or positioning. While the device has been presented herein as a single anchor, it may be used in pairs within a lumen to trap a marker between the pair of anchors. As long as the marker cannot escape through the LRD device toward to the larger bronchiole structures the device should remains stationary and the goal will be realized.

Consideration should be allowed for delivery of any of the devices as well. The ability of a device to be delivered in a compact, or compressed state, is a definite advantage. Further, the ability of a device to compensate for differences in lumen size and elasticity allows the use of a single device for a plurality of lumen sizes and, therefore, lumen locations. To fixate a marker within a lumen, the marker can be forcibly wedged within the lumen, anchored to the luminal wall, entrapped against the luminal wall, anchored to the luminal wall using a leg of a bifurcation point, entrapped within the lumen by a second device, or trapped at a specific location within the lumen by the use of two secondary devices. Combinations of these methods may be employed as well.

B. Catheter having a Preloaded Marker Positioned at a Distal End

Figure 1B:
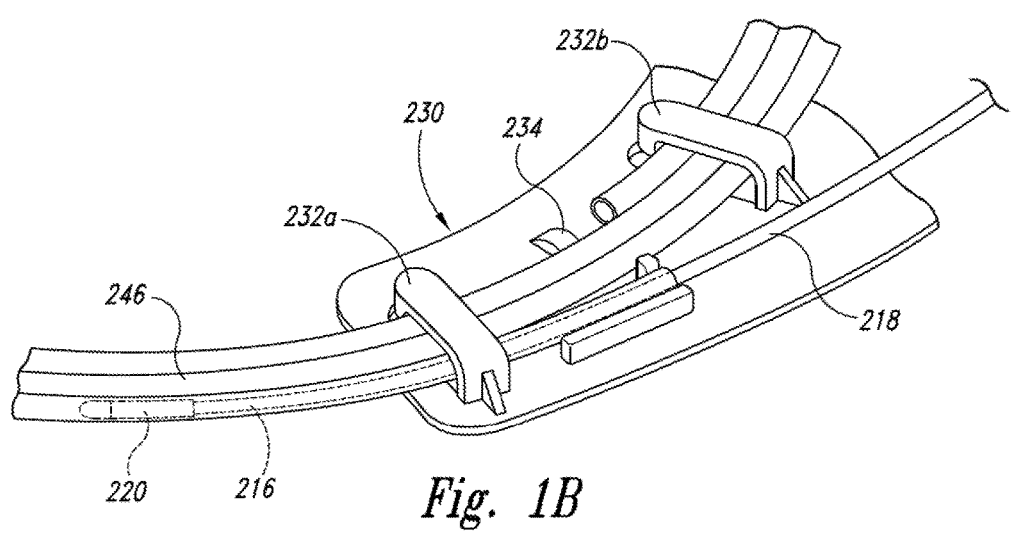
FIG. 1B is an enlarged isometric view of the bronchoscopic catheter assembly of FIG. 1A with a marker loaded in the catheter assembly configured in accordance with an embodiment of the present technology.
Figure 1C:
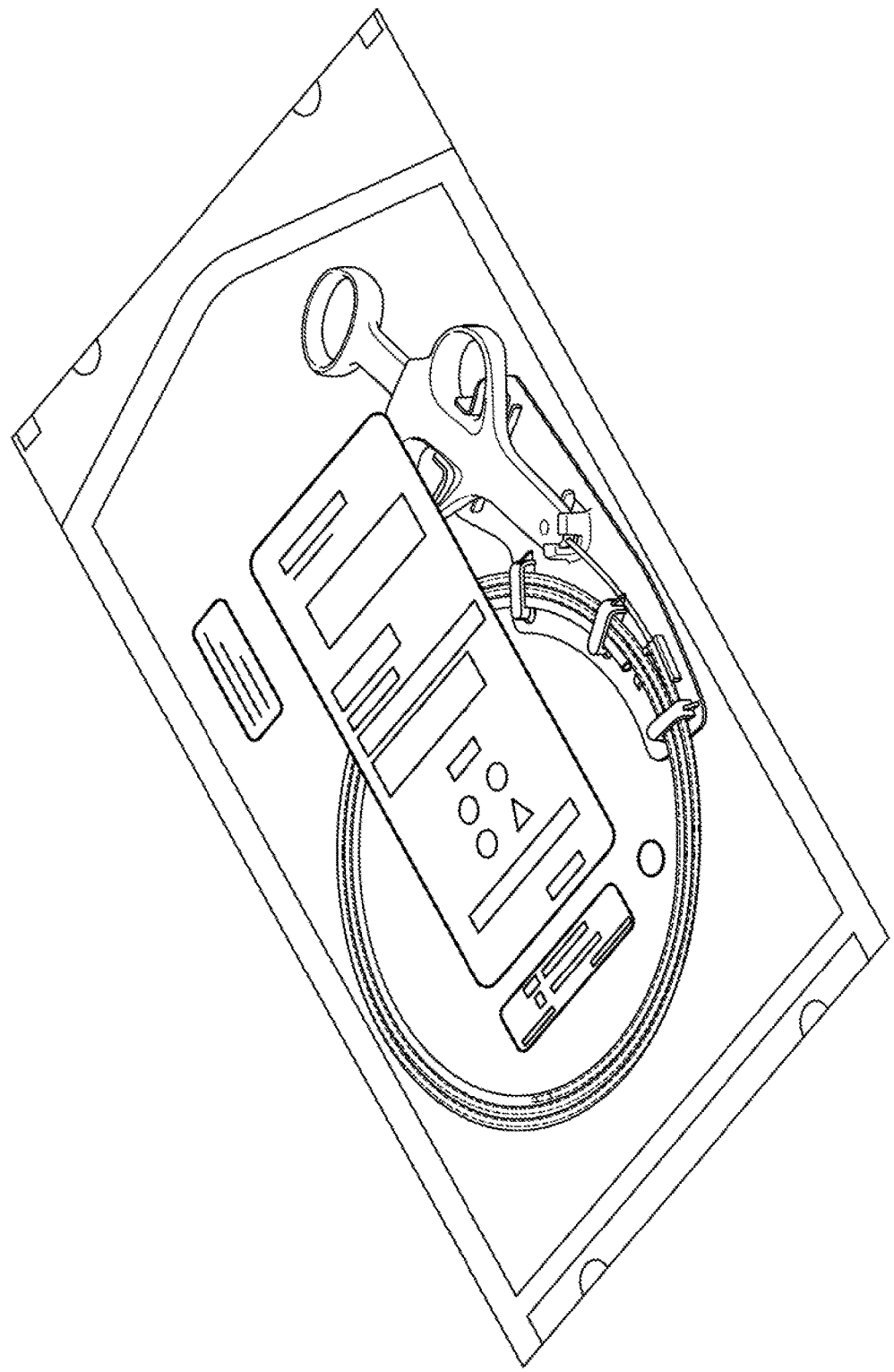
FIGS. 1C and 1D are an isometric view and an exploded isometric view, respectively, of a package carrying the bronchoscopic catheter assembly of FIGS. 1A and 1B in accordance with an embodiment of the present technology.
Figure 1D:
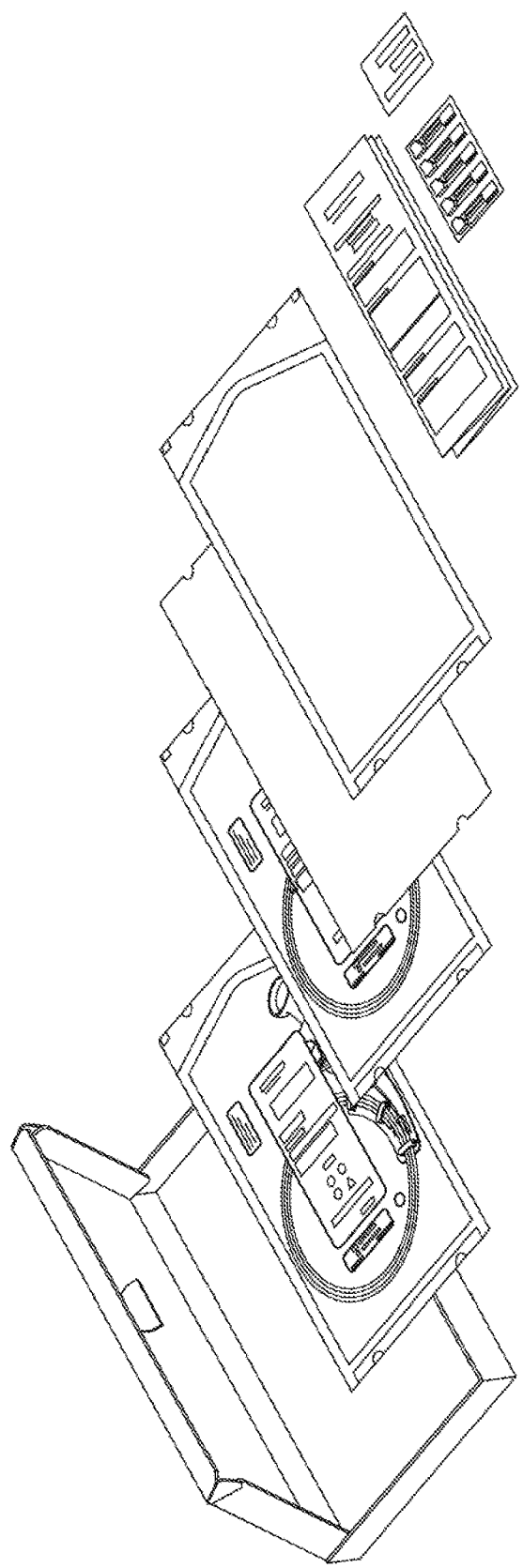

FIG. 1A is an isometric view of a bronchoscopic catheter assembly 200 for use in a working channel of a bronchoscope (not shown for clarity) and a storage and transportation device 240 having a receiving hoop 246 for releasably retaining a delivery catheter 212 during storage and transportation of the delivery catheter 212 in accordance with an embodiment of the invention. FIG. 1B is an isometric, expanded view of the bronchoscopic catheter assembly 200 of FIG. 1A with a marker 220 loaded in the distal end 216 of the delivery catheter 212 and the storage and transportation device 240 cut away to show loading of the delivery catheter 212 in the receiving hoop 246. As shown in FIGS. 1A and 1B, the bronchoscopic catheter assembly 200 includes a delivery catheter 212 having a deployment channel 211 configured to releasably retain a marker 220 at a distal end 214 of the delivery catheter 212 such that the marker 220 extends a selected distance beyond a distal end 216 of the delivery catheter 212.

Referring now to FIG. 1A, the storage and transportation device 240 for retaining the bronchoscopic catheter assembly 200 during storage and transportation is provided. The storage and transportation device 240 includes a receiving hoop 246 for releasably retaining the delivery catheter 212. The storage and transportation device 240 can include a housing 230 which is configured to releasably retain the receiving hopp in clips 232a, b. The housing 230 may further include a guide 234 and/or an insertion guide assembly for guiding the distal end of the delivery catheter 212 therein. The housing 244 additionally provides an alignment means for mating with the distal end of the catheter when loading the marker 220 into the catheter as discussed further with respect to FIG. 5.

Referring now to FIG. 1A, a proximal end 214 of the delivery catheter 212 is configured to engage a handle 210 having an actuator 222. The actuator 222 is moveable between a first position and a second position along arrow A. In the second position, the actuator 222 moves towards and/or abuts a flange 224. The flange 224 is configured to stop movement of the actuator 222 along line A by engaging the actuator 222 on a first side. On a second side, opposite the first side, the flange 224 retains the delivery catheter 212. The flange 224 further includes a sleeve (not shown) for slidably receiving a push wire 218 therein.

The push wire 218 is retained by the body of the catheter and moves with the actuator 222. The push wire 218 may be a Teflon wire, steel cable, steel wire, Nitanol® or other flexible cable having sufficient rigidity to deploy the marker 220 when the actuator 222 is moved along line A. As shown in FIG. 3B, the push wire 218 may include a disc shaped end 404 for engaging the marker 220. Alternatively, an end 404 of the push wire 218 may be an appropriately shaped wire or rod. The end 404 may have a diameter dimension slightly less than the diameter dimension of the channel 211 to allow the push wire 218 to slide co-axially therein. The distal end of the delivery catheter is described in greater detail below.

Figure 2:
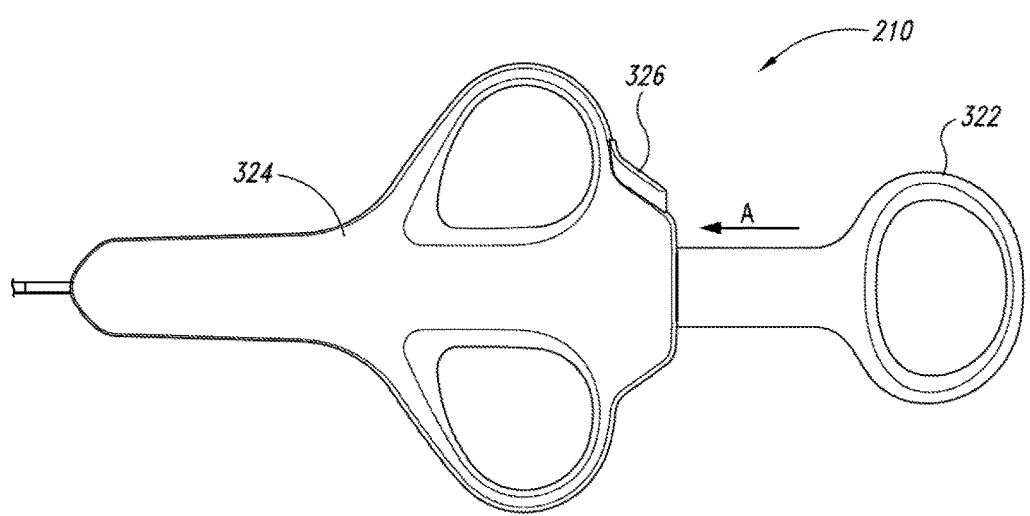
FIG. 2 is a side view of a handle configured in accordance an embodiment of the present technology.

The handle 210 is configured to be moveable by an operator (not shown) and may further be configured to attach to the working channel of the bronchoscope. Referring now to FIG. 2, the handle 210 can include an actuator 322 including a button or flat plate configured to be engaged by a digit of an operator's hand (not shown for purposes of clarity). The actuator 322 abuts the housing 324 to stop axial movement along line A. As shown in FIG. 2, the handle 210 can include an actuator 322 including a ring configured to be engaged by a digit of an operator's hand. As further shown, the housing 326 can be ergonomically shaped to the hand of a user. Alternative configurations of the actuator can further be provided. The handle 210 may further include a lock 326, shown in FIG. 2 on the housing 324, to prevent accidental deployment of the marker.

One aspect of several embodiments of the present invention is delivering or deploying the markers 40 into or at least proximate to a tumor located in the lung of the patient. Accordingly, the delivery device can be a bronchoscope, catheter, or other device configured to pass through a lumen in the respiratory system of the patient. Generally speaking, the delivery device includes a handle and an elongated body attached to the handle. More specifically, the elongated body includes a proximal section at the handle and a distal section configured to pass through lumen in the respiratory system. In many embodiments, the distal section of the elongated body is flexible, but in other embodiments the entire elongated body can be flexible or rigid. In operation, the marker is supported by the elongated body at the distal section for deployment into the patient. In several embodiments, the delivery device further includes a deployment mechanism that is operable from the handle to release the marker into the patient. The deployment mechanism can be a push rod that pushes the marker out of the distal section of the elongated body. In an alternative embodiment, the deployment mechanism can include a cannula and a stylet slidably received in the cannula. In this embodiment, the cannula and stylet are configured to move together to project distally beyond the distal section of the elongated body, and then the cannula may be withdrawn proximally relative to the stylet to release the marker into the patient.

According to still further embodiments, the delivery device can further include a steering mechanism that is operable from the handle. The steering mechanism can include an attachment point at the distal section and a slidable member configured to move longitudinally relative to the elongated body. Longitudinal movement of the slidable member flexes the distal section in a manner that steers the delivery device through bends and bifurcations in the lumen of the respiratory system. In other embodiments, the steering mechanism comprises a flexible support element and a flexible control element attached to the flexible support element such that tension applied to the control element flexes the flexible support element. Suitable steering mechanisms are set forth in U.S. Pat. No. 6,702,780 and U.S. Patent Application Publication No. US 2003/0208101 A1, both of which are incorporated herein by reference.

Figure 1E:
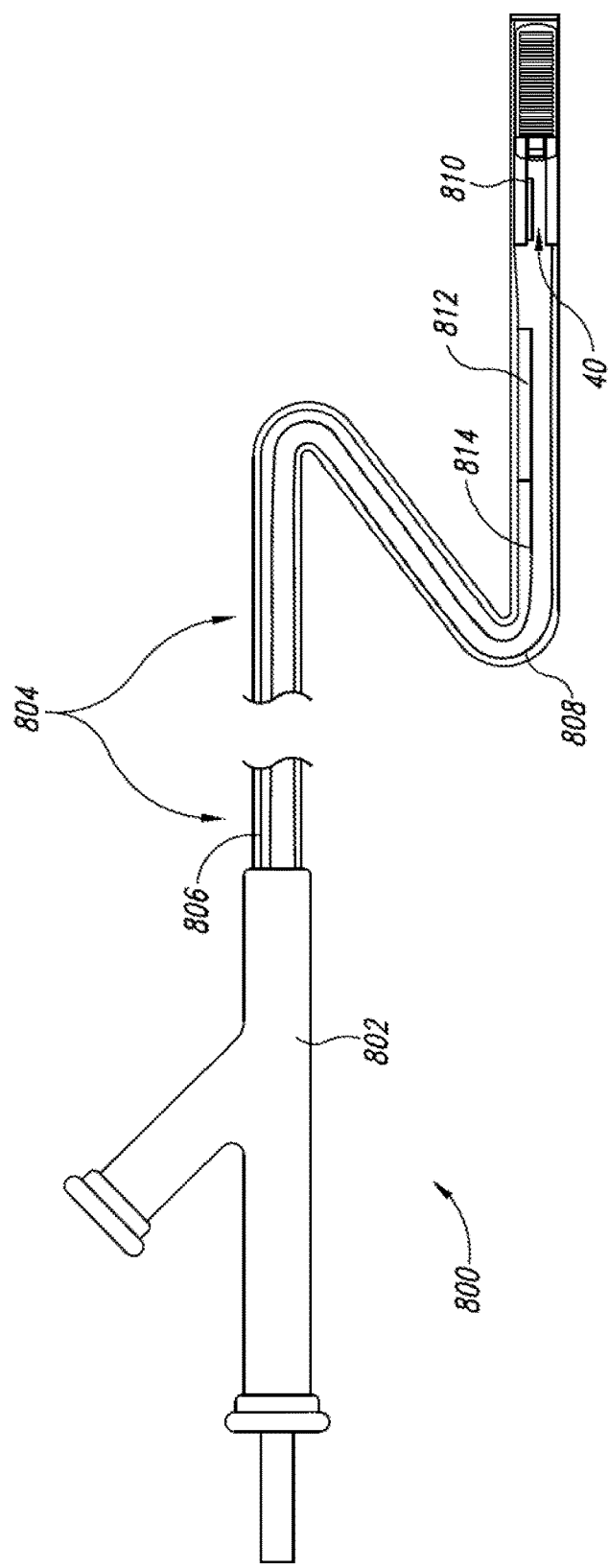
FIG. 1E is a partial cut-away side view of a delivery device configured in accordance an embodiment of the present technology.

FIG. 1E is an isometric view of a delivery device 820 in accordance with another embodiment of the invention. The delivery device 820 can be a needle or other type of introducer for percutaneously implanting the marker 40 into the lung of the patient trans-thoracically. The delivery device 820 includes a handle 822, a slider 824 received in the handle 822, and an actuator 826 attached to the slider 824. The delivery device 820 further includes a cannula 828 attached to the slider 824 and a stylet 829 fixedly attached to the handle 822. In operation, the cannula 828 and stylet 829 are percutaneously inserted into the patient. When the marker 40 is at a desired location relative to the target, the actuator 826 is drawn proximately to move the slider 824 proximally within the handle 822. This motion withdraws the cannula 828 over the stylet 829 to release the marker 40 in the patient. The delivery device 820 and several other embodiments of delivery devices for percutaneous implantation of the markers are described in U.S. Patent Application No. 60/590,521 and U.S. Pat. No. 7,247,160, both of which are incorporated herein by reference in their entirety.

Figure 3A:
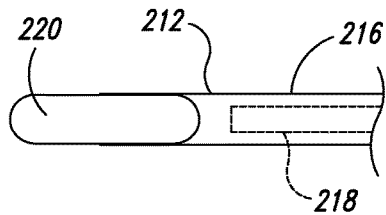
FIGS. 3A-3D are side views of a distal portion of a delivery catheter releasably retaining a marker in accordance with embodiments of the present technology.
Figure 3B:
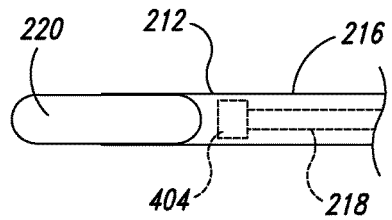
Figure 3C:
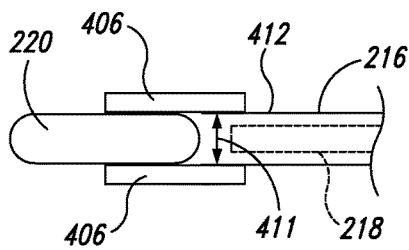

Referring now to FIGS. 3A-3D, the distal end 216 of the delivery catheter 212 releasably retains the marker 220. As shown in FIG. 3A, an outside diameter of the marker 220 can be approximately equal to the diameter of the channel 211. Alternatively, as shown in FIG. 3C, a sleeve 406 can be placed at a distal end 216 of the delivery catheter 412. An inside diameter of the sleeve 406 can be approximately equal to the outside diameter of the marker 220 and configured to releasably retain the marker 220. According to this embodiment, the channel 411 can have an inside diameter smaller than the outside diameter of the marker 220. The sleeve 406 may be made from a semi-rigid, rigid, or flexible material different from the catheter 412, or may be made from the same material as the catheter 412.

Figure 3D:
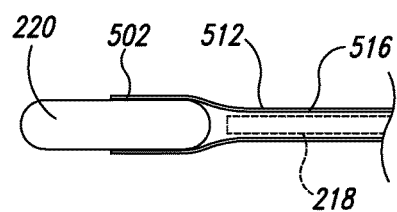

Referring now to FIG. 3D, the distal end 516 of the delivery catheter 512 releasably retains the marker 220 by expanding around the marker 220. According to aspects of this embodiment, the inside diameter of the delivery catheter 512 is less that the outside diameter of the marker 220. The delivery catheter 512 is made from a sufficiently flexible material to allow the delivery catheter 512 to expand around the marker 220 and releasably retain the marker 220 prior to deployment. Alternatively, another method besides compression fit to hold the marker in place is to use a material for example, coconut oil that is solid at room temperature and liquid at body temperature. Alternately, the material could be liquid soluble, such as sucrose or NaCl; exposure to the lumen would detach the marker.

Figure 4:
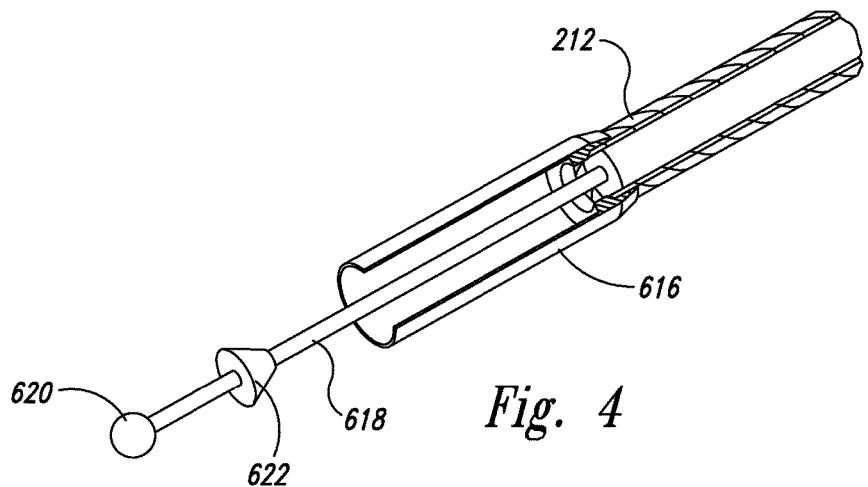
FIG. 4 is an isometric cut-away view of a distal portion of a delivery catheter configured in accordance an embodiment of the present technology.

Referring now to FIG. 4, a cut away schematic view of the distal end of a delivery catheter in accordance with an embodiment of the disclosure is shown. A retention sleeve 606 is placed at the distal end 616 of the delivery catheter 612. An inside diameter of the sleeve 606 can be approximately equal to the outside diameter of the marker. The deployment wire or push wire 618 includes an engagement member 620 and a deployment member 622. The engagement member 620 is positioned at a distal end of the push wire and is configured as a ball end in FIG. 4. Alternatively, the engagement member 620 may be a wedge, a plate or other geometric shape as appropriate. The deployment member 622 is positioned co-axially at a predetermined distance away from the distal end of the push wire. As will be understood by one skilled in the art, the deployment member 622 may be a tapered wedge as shown or may be any other geometric shape.

Figure 5:
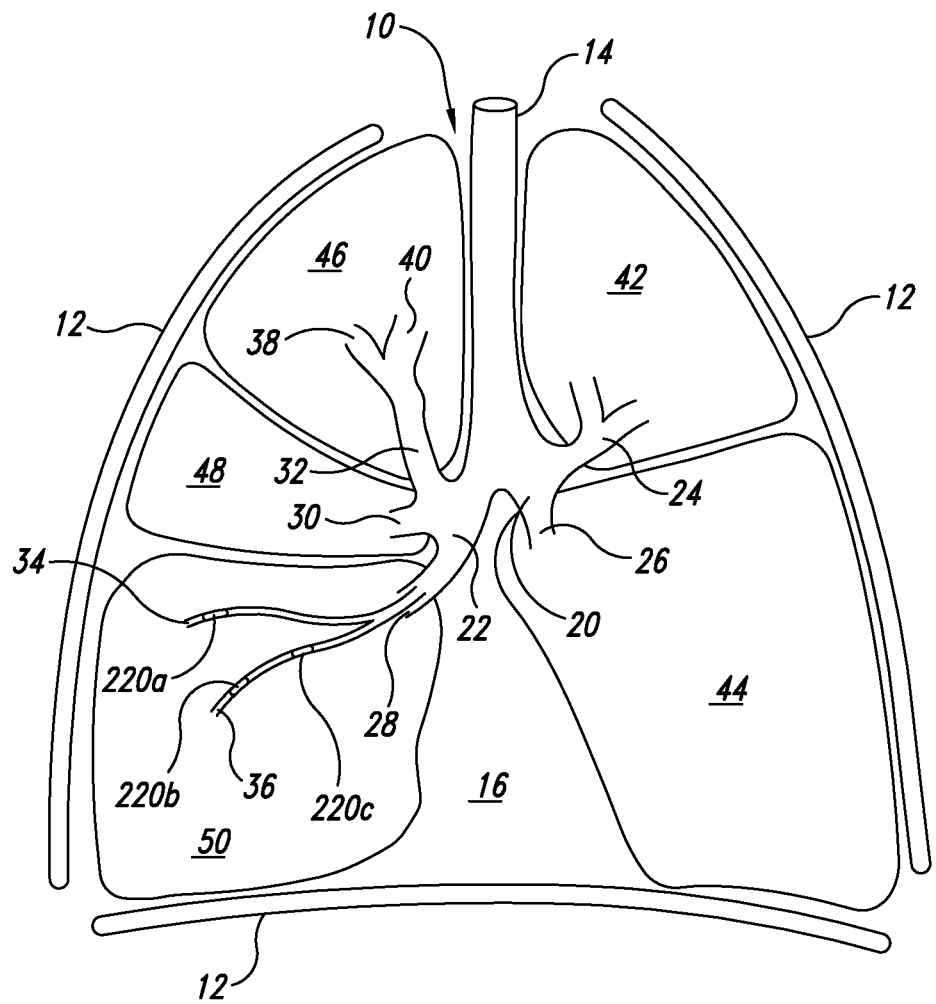
FIG. 5 is a cross-sectional view of a respiratory system having markers positioned therein in accordance with an embodiment of the present technology.

FIG. 5 is a cross-sectional view of an exemplary healthy respiratory system 110 having markers 220a-c positioned therein. The respiratory system 110 resides within a thorax 16 which occupies a space defined by a chest wall 12 and a diaphragm 13. The respiratory system 10 includes trachea 16; left mainstem bronchus 20 and right mainstem bronchus 22 (primary, or first generation); lobar bronchial branches 24, 26, 28, 30, 32, 38 and 40 (second generation), and segmental branches 34 and 36 (third generation). The respiratory system 10 further includes left lung lobes 42 and 44 and right lung lobes 46, 48 and 50. Each bronchial branch and sub-branch communicates with a different portion of a lung lobe, either the entire lung lobe or a portion thereof. As used herein, the term "passageway" is meant to denote either a bronchi or bronchioli, and typically means a bronchial branch of any generation.

As shown in FIG. 5, three transponders 220a-c are positioned in the respiratory system 110 of a patient in the proximity of a tumor or lesion 100. The transponders 220a-c are used to localize a patient target treatment isocenter relative to a linear accelerator machine isocenter as described further herein. As a process step during radiation therapy treatment planning, a patient undergoes a CT scan whereby the X, Y, and Z positions of the radiographic centers for all three transponders 220a-c as well as the X, Y, and Z position for the treatment target isocenter are identified. To localize a patient treatment target isocenter relative to the linear accelerator treatment target isocenter both prior to and during radiation therapy delivery, the three transponder positions that are positioned in the lung are localized electromagnetically and then used to calculate the position of the treatment target isocenter position and rotational offsets.

The markers 220a-c are placed in the respiratory system 110 by the bronchoscopic catheter assembly 200 as described further herein. The markers 220a-c are preferably a small alternating magnetic transponder. The transponders can each have a unique frequency relative to each other to allow for time and frequency multiplexing. The transponders can accordingly include a core, a coil wound around the core, and a capacitor electrically coupled to the coil. The bronchoscopic catheter assembly 200 can deploy one or more transponders, and as such is not limited to having three transponders as illustrated. The transponders are localized using a source, sensor array, receiver, and localization algorithm as described further herein.

In operation, the three transponders may be used to localize a treatment target isocenter relative to a linear accelerator radiation therapy treatment isocenter. The treatment target localization may include both translational offset (X, Y, and Z directions) and a rotational offset (pitch, yaw, and roll) relative to a linear accelerator coordinate reference frame.

C. Catheter Tip Configured to Reduce Pneumothorax

According to aspects of the invention, a distal end of a catheter is configured to reduce pneumothorax. The marker 220 is pre-loaded into the distal end 216 of the delivery catheter 212 such that a portion of the marker 220 extends beyond the distal end 216 of the delivery catheter 212, thus providing a rounded leading end of the delivery catheter 212. Providing a rounded leading end of the distal end of the delivery catheter 212 by pre-loading a cylindrical shaped marker, such as a transponder, reduces the puncture rate of the visceral pleura which can occur during bronchoscopic implantation, and thus reduces the likelihood of pneumothorax. Without being bound by theory, pre-loading the cylindrical shaped marker provides a rounded end shape to the delivery catheter 212; the rounded end shape keeps the delivery catheter 212 centered in the passageway. The rounded leading end also maximizes the surface area of tissue (e.g. visceral pleura) that the distal end of the catheter contacts. The catheter distal end is thus less likely to cut through tissue since it maximizes tissue surface area contact by incorporating a smooth rounded tip that does not include any edges that could concentrate force facilitate tissue perforation.

D. Radiation Therapy Systems with Real-Time Tracking Systems

Figure 6:
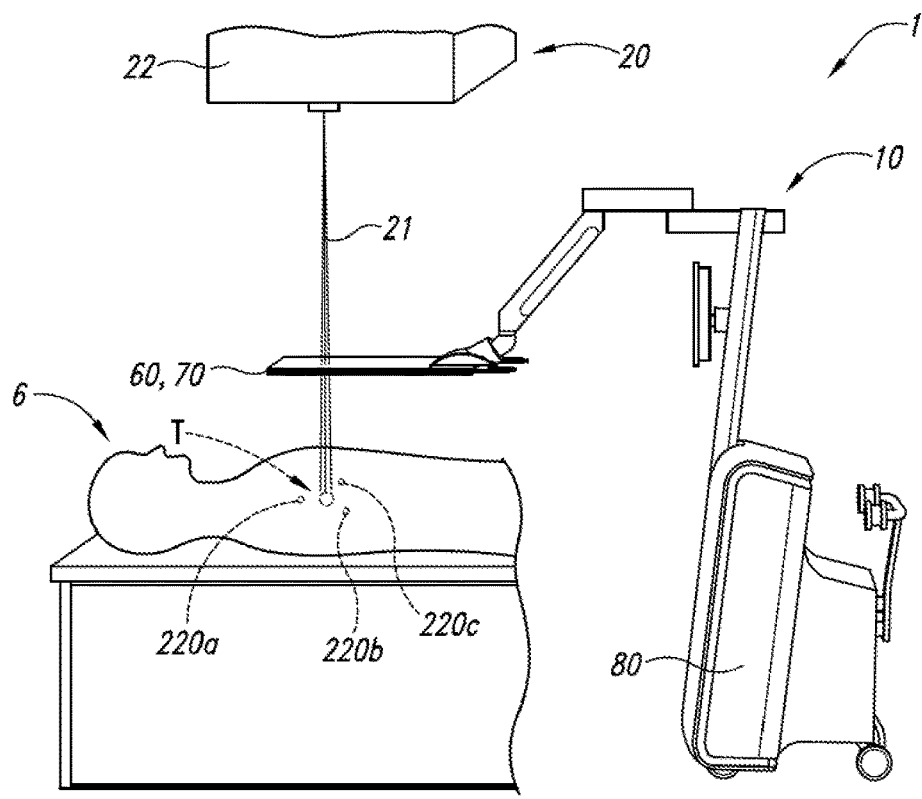
FIGS. 6 and 7 are isometric and side views of various aspects of a radiation therapy system configured in accordance an embodiment of the present technology.
Figure 7:
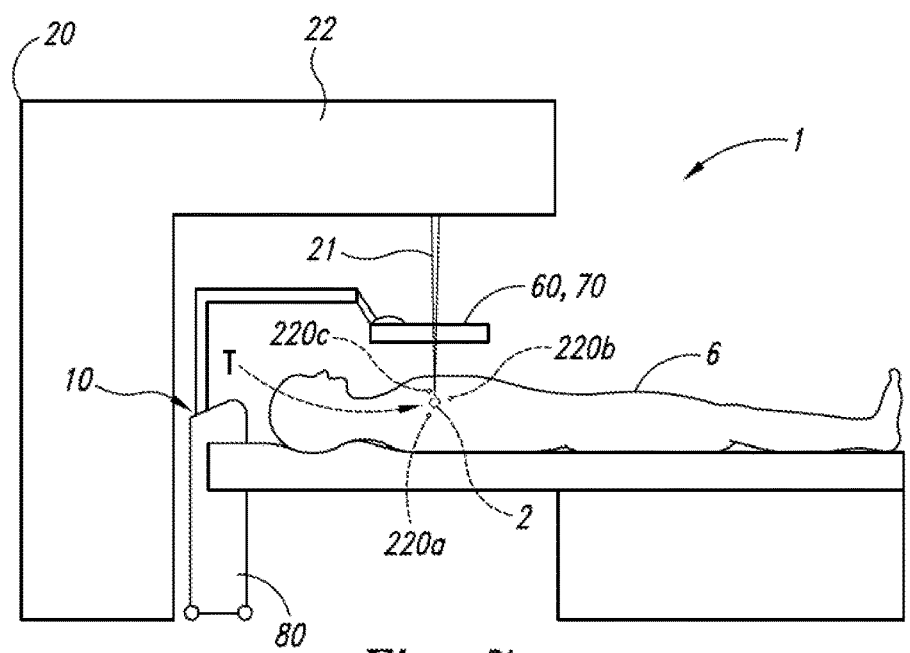

FIGS. 6 and 7 illustrate various aspects of a radiation therapy system 1 for applying guided radiation therapy to a target 2 (e.g., a tumor) within a lung or other part of a patient 6. The radiation therapy system 1 has a localization system 10 and a radiation delivery device 20. The localization system 10 is a tracking unit that locates and tracks the actual position of the target 2 in real time during treatment planning, patient setup, and/or while applying ionizing radiation to the target from the radiation delivery device. Moreover, the localization system 10 continuously tracks the target and provides objective data (e.g., three-dimensional coordinates in an absolute reference frame) to a memory device, user interface, linear accelerator, and/or other device. The system 1 is described below in the context of guided radiation therapy for treating a tumor or other target in the lung of the patient, but the system can be used for tracking and monitoring other targets within the patient for other therapeutic and/or diagnostic purposes.

The radiation delivery source of the illustrated embodiment is an ionizing radiation device 20 (i.e., a linear accelerator). Suitable linear accelerators are manufactured by Varian Medical Systems, Inc. of Palo Alto, Calif.; Siemens Medical Systems, Inc. of Iselin, N.J.; Elekta Instruments, Inc. of Iselin, N.J.; or Mitsubishi Denki Kabushik Kaisha of Japan. Such linear accelerators can deliver conventional single or multi-field radiation therapy, 3D conformal radiation therapy (3D CRT), IMRT, stereotactic radiotherapy, and tomo therapy. The radiation delivery device 20 can deliver a gated, contoured, or shaped beam 21 of ionizing radiation from a movable gantry 22 to an area or volume at a known location in an external, absolute reference frame relative to the radiation delivery device 20. The point or volume to which the ionizing radiation beam 21 is directed is referred to as the machine isocenter.

The tracking system includes the localization system 10 and one or more markers 220. The localization system 10 determines the actual location of the markers 220 in a three-dimensional reference frame, and the markers 220 are typically within the patient 6. In the embodiment illustrated in FIGS. 6 and 7, more specifically, three markers identified individually as markers 220a-c are implanted in the lung of the patient 6 at locations in or near the target 2. In other applications, a single marker, two markers, or more than three markers can be used depending upon the particular application. The markers 220 are desirably placed relative to the target 2 such that the markers 220 are at least substantially fixed relative to the target 2 (e.g., the markers move at least in direct proportion to the movement of the target). As discussed above, the relative positions between the markers 220 and the relative positions between a target isocenter T of the target 2 and the markers 220 can be determined with respect to an external reference frame defined by a CT scanner or other type of imaging system during a treatment planning stage before the patient is placed on the table. In the particular embodiment of the system 1 illustrated in FIGS. 6 and 7, the localization system 10 tracks the three-dimensional coordinates of the markers 220 in real time relative to an absolute external reference frame during the patient setup process and while irradiating the patient to mitigate collateral effects on adjacent healthy tissue and to ensure that the desired dosage is applied to the target.

E. General Aspects of Markers and Localization Systems

Figure 8:
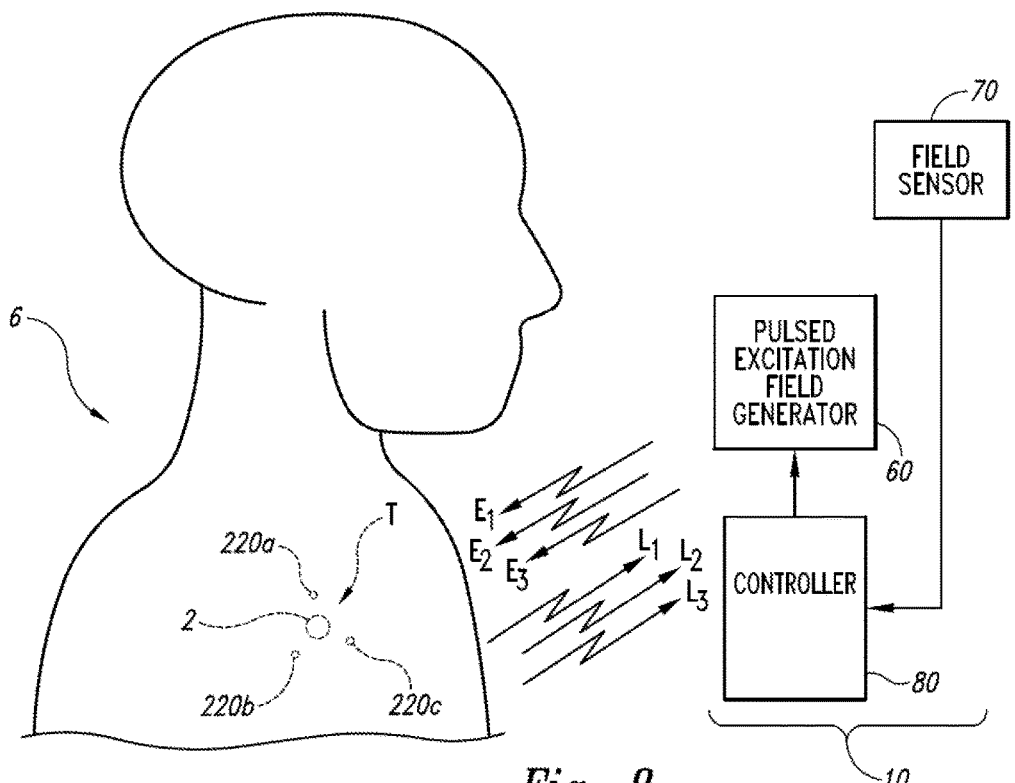
FIG. 8 is a schematic view illustrating operation of a localization system and markers in accordance with an embodiment of the present technology.

FIG. 8 is a schematic view illustrating the operation of an embodiment of the localization system 10 and markers 220*a-c* for treating a tumor or other target in the lung of the patient. The localization system 10 and the markers 220*a-c* are used to determine the location of the target 2 (FIGS. 6 and 7) before, during, and after radiation sessions. More specifically, the localization system 10 determines the locations of the markers 220*a-c* and provides objective target position data to a memory, user interface, linear accelerator, and/or other device in real time during setup, treatment, deployment, simulation, surgery, and/or other medical procedures.

In one embodiment of the localization system, real time means that indicia of objective coordinates are provided to a user interface at (a) a sufficiently high refresh rate (i.e., frequency) such that pauses in the data are not humanly discernable and (b) a sufficiently low latency to be at least substantially contemporaneous with the measurement of the location signal. In other embodiments, real time is defined by higher frequency ranges and lower latency ranges for providing the objective data to a radiation delivery device, or in still other embodiments real time is defined as providing objective data responsive to the location of the markers (e.g., at a frequency that adequately tracks the location of the target in real time and/or a latency that is substantially contemporaneous with obtaining position data of the markers).

1. Localization Systems

The localization system 10 includes an excitation source 60 (e.g., a pulsed magnetic field generator), a sensor assembly 70, and a controller 80 coupled to both the excitation source 60 and the sensor assembly 70. The excitation source 60 generates an excitation energy to energize at least one of the markers 220*a-c* in the patient 6 (FIG. 6). The embodiment of the excitation source 60 shown in FIG. 8 produces a pulsed magnetic field at different frequencies. For example, the excitation source 60 can frequency multiplex the magnetic field at a first frequency E1 to energize the first marker 220*a*, a second frequency E2 to energize the second marker 220*b*, and a third frequency E3 to energize the third marker 220*c*. In response to the excitation energy, the markers 220*a-c* generate location signals L1-3 at unique response frequencies. More specifically, the first marker 220*a* generates a first location signal L1 at a first frequency in response to the excitation energy at the first frequency E1, the second marker 220*b* generates a second location signal L2 at a second frequency in response to the excitation energy at the second frequency E2, and the third marker 220*c* generates a third location signal L3 at a third frequency in response to the excitation energy at the third frequency E3. In an alternative embodiment with two markers, the excitation source generates the magnetic field at frequencies E1 and E2, and the markers 220*a-b* generate location signals L1 and L2, respectively.

The sensor assembly 70 can include a plurality of coils to sense the location signals L1-3 from the markers 220*a-c*. The sensor assembly 70 can be a flat panel having a plurality of coils that are at least substantially coplanar relative to each other. In other embodiments, the sensor assembly 70 may be a non-planar array of coils.

The controller 80 includes hardware, software, or other computer-operable media containing instructions that operate the excitation source 60 to multiplex the excitation energy at the different frequencies E1-3. For example, the controller 80 causes the excitation source 60 to generate the excitation energy at the first frequency E1 for a first excitation period, and then the controller 80 causes the excitation source 60 to terminate the excitation energy at the first frequency E1 for a first sensing phase during which the sensor assembly 70 senses the first location signal L1 from the first marker 220*a* without the presence of the excitation energy at the first frequency E1. The controller 80 then causes the excitation source 60 to: (a) generate the second excitation energy at the second frequency E2 for a second excitation period; and (b) terminate the excitation energy at the second frequency E2 for a second sensing phase during which the sensor assembly 70 senses the second location signal L2 from the second marker 220*b* without the presence of the second excitation energy at the second frequency E2. The controller 80 then repeats this operation with the third excitation energy at the third frequency E3 such that the third marker 220*c* transmits the third location signal L3 to the sensor assembly 70 during a third sensing phase. As such, the excitation source 60 wirelessly transmits the excitation energy in the form of pulsed magnetic fields at the resonant frequencies of the markers 220*a-c* during excitation periods, and the markers 220*a-c* wirelessly transmit the location signals L1-3 to the sensor assembly 70 during sensing phases. It will be appreciated that the excitation and sensing phases can be repeated to permit averaging of the sensed signals to reduce noise.

The computer-operable media in the controller 80, or in a separate signal processor, or other computer also includes instructions to determine the absolute positions of each of the markers 220*a-c* in a three-dimensional reference frame. Based on signals provided by the sensor assembly 70 that correspond to the magnitude of each of the location signals L1-3, the controller 80 and/or a separate signal processor calculates the absolute coordinates of each of the markers 220*a-c* in the three-dimensional reference frame. The absolute coordinates of the markers 220*a-c* are objective data that can be used to calculate the coordinates of the target in the reference frame. When multiple markers are used, the rotation of the target can also be calculated.

2. Real-Time Tracking

The localization system 10 and at least one marker 220 enable real-time tracking of the target 2 relative to the machine isocenter or another external reference frame outside of the patient during treatment planning, setup, radiation sessions, and at other times of the radiation therapy process. In many embodiments, real-time tracking means collecting position data of the markers, determining the locations of the markers in an external reference frame, and providing an objective output in the external reference frame that is responsive to the location of the markers. The objective output is provided at a frequency that adequately tracks the target in real time and/or a latency that is at least substantially contemporaneous with collecting the position data (e.g., within a generally concurrent period of time).

For example, several embodiments of real-time tracking are defined as determining the locations of the markers and calculating the location of the target relative to the machine isocenter at (a) a sufficiently high frequency so that pauses in representations of the target location at a user interface do not interrupt the procedure or are readily discernable by a human, and (b) a sufficiently low latency to be at least substantially contemporaneous with the measurement of the location signals from the markers. Alternatively, real time means that the localization system 10 calculates the absolute position of each individual marker 220 and/or the location of the target at a periodicity of 1 ms to 5 seconds, or in many applications at a periodicity of approximately 10-100 ms, or in some specific applications at a periodicity of approximately 20-50 ms. In applications for user interfaces, for example, the periodicity can be 12.5 ms (i.e., a frequency of 80 Hz), 16.667 ms (60 Hz), 20 ms (50 Hz), and/or 50 ms (20 Hz).

Alternatively, real-time tracking can further mean that the localization system 10 provides the absolute locations of the markers 220 and/or the target 2 to a memory device, user interface, linear accelerator, or other device within a latency of 10 ms to 5 seconds from the time the localization signals were transmitted from the markers 220. In more specific applications, the localization system generally provides the locations of the markers 220 and/or target 2 within a latency of about 20-50 ms. The localization system 10 accordingly provides real-time tracking to monitor the position of the markers 220 and/or the target 2 with respect to an external reference frame in a manner that is expected to enhance the efficacy of radiation therapy because higher radiation doses can be applied to the target and collateral effects to healthy tissue can be mitigated.

The system described herein uses one or more markers to serve as registration points to characterize target location, rotation, and motion. In accordance with aspects of the invention, the markers have a substantially fixed relationship with the target. If the markers did not have a substantially fixed relationship with the target, another type of tracking error would be incurred. This generally requires the markers to be fixed or positioned sufficiently close to the target in order that tracking errors be within clinically meaningful limits; thus, the markers may be placed in tissue or bone that exhibits representative motion of the target. For example, with respect to the lung, a device that is representative of the target's motion would include a marker retained in bronchi of a patient.

According to aspects of the present invention, the marker motion is a surrogate for the motion of the target. Accordingly, the marker is placed such that it moves in direct correlation to the target being tracked. Depending on the target being tracked, the direct correlation relationship between the target and the marker will vary. For example, with respect to soft tissue that moves substantially in response to the respirations of the patient, such as the lung, the marker may be placed in a bronchi to provide surrogate motion in direct correlation with target motion.

Figure 9:
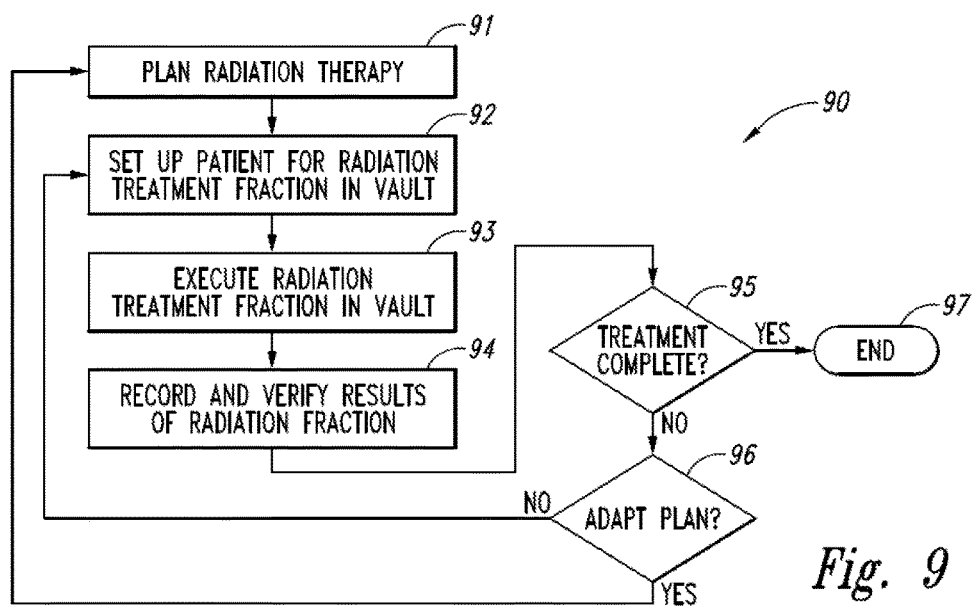
FIG. 9. is a flow diagram for real-time tracking to monitor location and status of a target in accordance with an embodiment of the present technology.
Figure 10A:
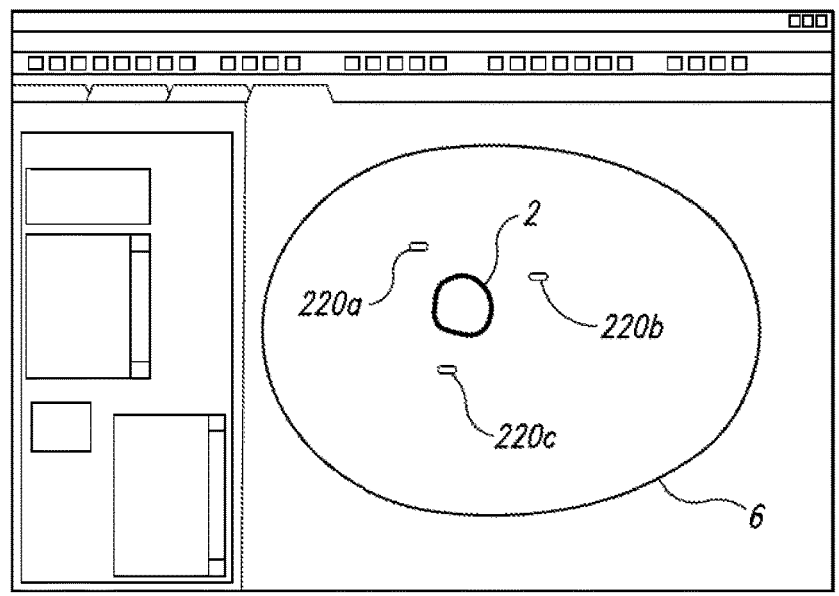
FIG. 10A is a CT image illustrating a cross-section of a patient, a target, and a marker in accordance with an embodiment of the present technology.
Figure 10B:
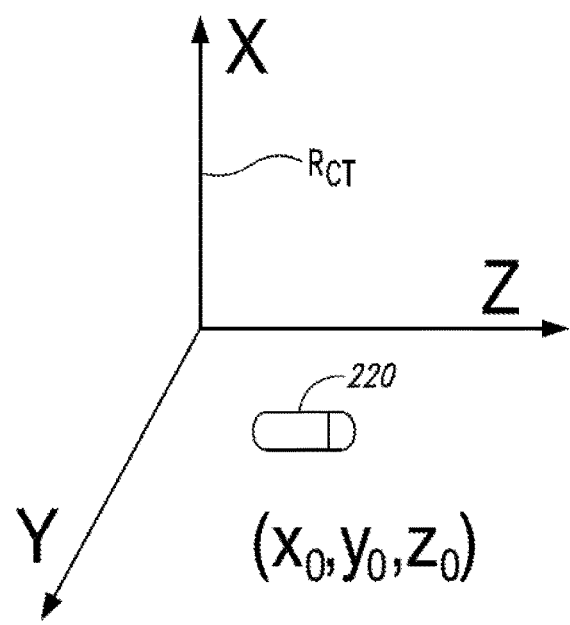
FIG. 10B illustrates coordinates of the marker in a reference frame of the CT scanner.

FIG. 9 is a flow diagram illustrating several aspects and uses of real-time tracking to monitor the location and the status of the target. In this embodiment, an integrated method 90 for radiation therapy includes a radiation planning procedure 91 that determines the plan for applying the radiation to the patient over a number of radiation fractions. The radiation planning procedure 91 typically includes an imaging stage in which images of a tumor or other types of targets are obtained using X-rays, CT, MR, or ultrasound imaging. The images are analyzed by a person to measure the relative distances between the markers and the relative position between the target and the markers. FIG. 10A, for example, is a representation of a CT image showing a cross-section of the patient 6, the target 2, and a marker 220. Referring to FIG. 10B, the coordinates (x0, y0, z0) of the marker 220 in a reference frame RCT of the CT scanner can be determined by an operator. The coordinates of the tumor can be determined in a similar manner to ascertain the offset between the marker and the target. Alternatively, the coordinates of a radiographic fiducial 30 in a reference frame RCT of the CT scanner can be determined by an operator.

Figure 11:
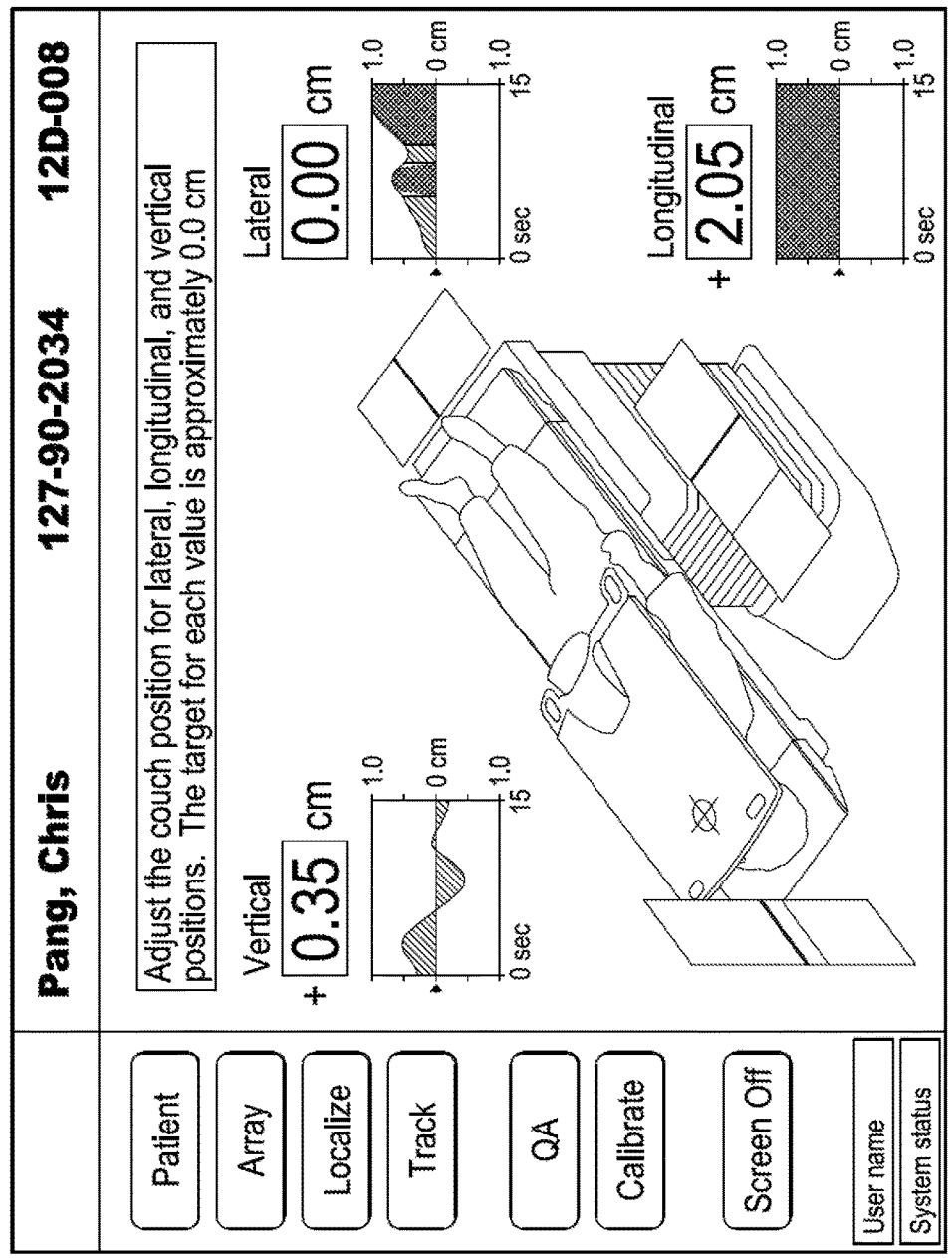
FIG. 11 illustrates a user interface showing objective offset values of a target relative to a machine isocenter in accordance with an embodiment of the present technology.

The localization system 10 and the markers 220 enable an automated patient setup process for delivering the radiation. After developing a treatment plan, the method 90 includes a setup procedure 92 in which the patient is positioned on a movable support table so that the target and markers are generally adjacent to the sensor assembly. As described above, the excitation source is activated to energize the markers, and the sensors measure the strength of the signals from the markers. The computer controller then (a) calculates objective values of the locations of the markers and the target relative to the machine isocenter, and (b) determines an objective offset value between the position of the target and the machine isocenter. Referring to FIG. 11, for example, the objective offset values can be provided to a user interface that displays the vertical, lateral, and longitudinal offsets of the target relative to the machine isocenter. A user interface may, additionally or instead, display target rotation.

One aspect of several embodiments of the localization system 10 is that the objective values are provided to the user interface or other device by processing the position data from the field sensor 70 in the controller 80 or other computer without human interpretation of the data received by the sensor assembly 70. If the offset value is outside of an acceptable range, the computer automatically activates the control system of the support table to move the tabletop relative to the machine isocenter until the target isocenter is coincident with the machine isocenter. The computer controller generally provides the objective output data of the offset to the table control system in real time as defined above. For example, because the output is provided to the radiation delivery device, it can be at a high rate (1-20 ms) and a low latency (10-20 ms). If the output data is provided to a user interface in addition to or in lieu of the table controller, it can be at a relatively lower rate (20-50 ms) and higher latency (50-200 ms).

In one embodiment, the computer controller also determines the position and orientation of the markers relative to the position and orientation of simulated markers. The locations of the simulated markers are selected so that the target will be at the machine isocenter when the real markers are at the selected locations for the simulated markers. If the markers are not properly aligned and oriented with the simulated markers, the support table is adjusted as needed for proper marker alignment. This marker alignment properly positions the target along six dimensions, namely X, Y, Z, pitch, yaw, and roll. Accordingly, the patient is automatically positioned in the correct position and rotation relative to the machine isocenter for precise delivery of radiation therapy to the target.

Figure 12:
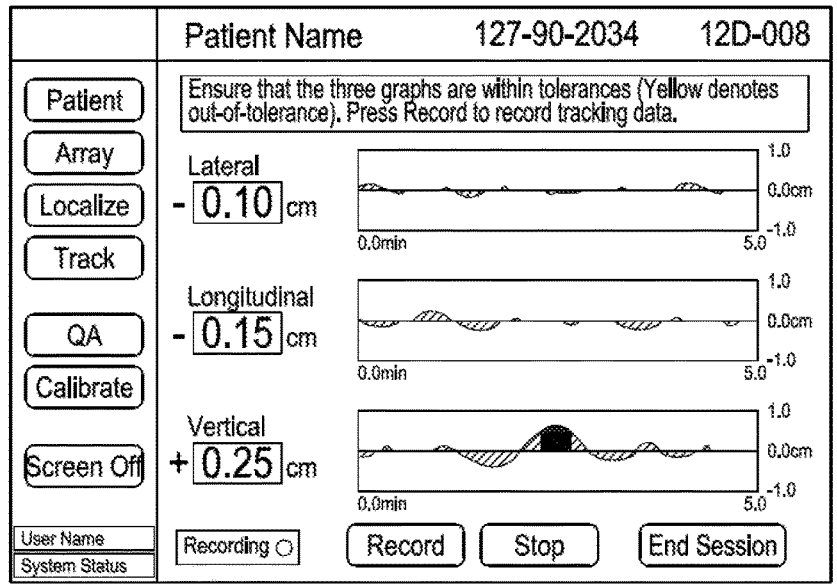
FIG. 12 illustrates a localization system tracking a target during a radiation session and controlling a radiation delivery source in accordance with an embodiment of the present technology.
Figure 12:
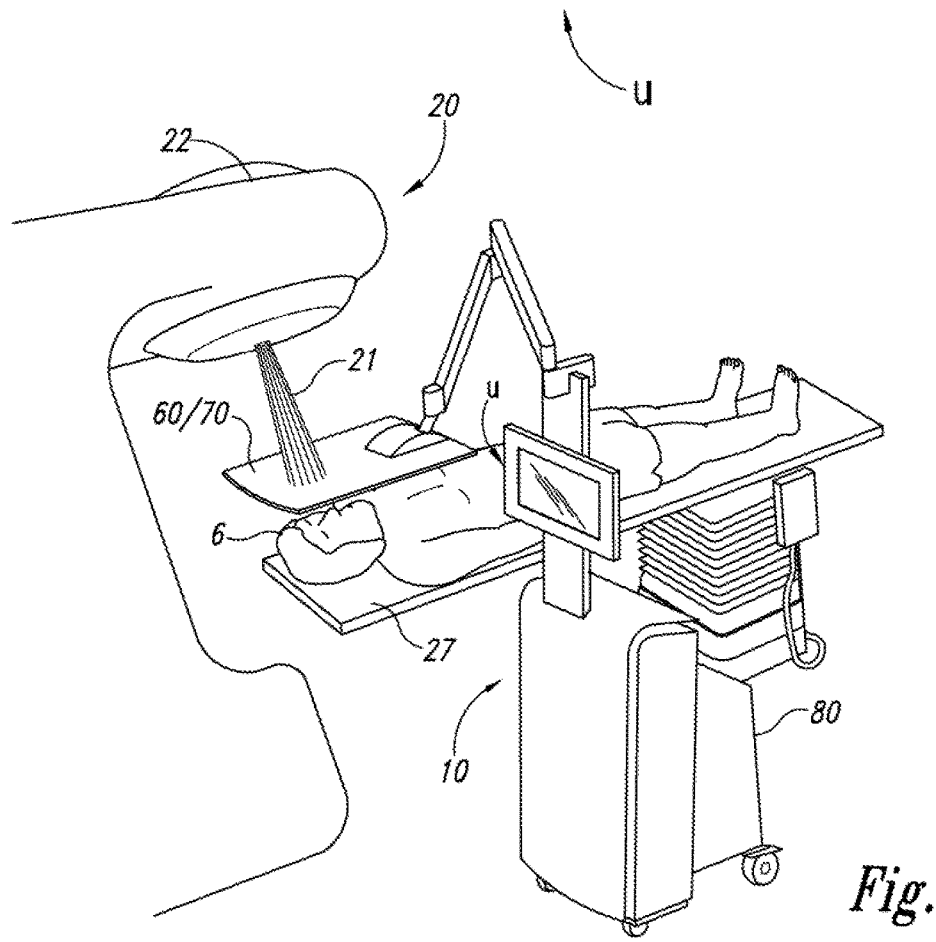

Referring back to FIG. 9, the method 90 further includes a radiation session 93. FIG. 12 shows a further aspect of an automated process in which the localization system 10 tracks the target during the radiation session 93 and controls the radiation delivery source 20 according to the offset between the target and the machine isocenter. For example, if the position of the target is outside of a permitted degree or range of displacement from the machine isocenter, the localization system 10 sends a signal to interrupt the delivery of the radiation or prevent initial activation of the beam. In another embodiment, the localization system 10 sends signals to automatically reposition a table 27 and the patient 6 (as a unit) so that the target isocenter remains within a desired range of the machine isocenter during the radiation session 93 even if the target moves. In still another embodiment, the localization system 10 sends signals to activate the radiation only when the target is within a desired range of the machine isocenter (e.g., gated therapy). In some embodiments, the localization system enables dynamic adjustment of the table 27 and/or the beam 21 in real time while irradiating the patient. Dynamic adjustment of the table 27 ensures that the radiation is accurately delivered to the target without requiring a large margin around the target.

The localization system 10 provides the objective data of the offset and/or rotation to the linear accelerator and/or the patient support table in real time as defined above. For example, as explained above with respect to automatically positioning the patent support table during the setup procedure 92, the localization system generally provides the objective output to the radiation delivery device at least substantially contemporaneously with obtaining the position data of the markers and/or at a sufficient frequency to track the target in real time. The objective output, for example, can be provided at a short periodicity (1-20 ms) and a low latency (10-20 ms) such that signals for controlling the beam 21 can be sent to the radiation delivery source 20 in the same time periods during a radiation session. In another example of real-time tracking, the objective output is provided a plurality of times during an "on-beam" period (e.g., 2, 5, 10, or more times while the beam is on). In the case of terminating or activating the radiation beam, or adjusting the leaves of a beam collimator, it is generally desirable to maximize the refresh rate and minimize the latency. In some embodiments, therefore, the localization system may provide the objective output data of the target location and/or the marker locations at a periodicity of 10 ms or less and a latency of 10 ms or less. The method 90 may further include a verification procedure 94 in which objective output data from the radiation session 93 is compared to the status of the parameters of the radiation beam.

The method 90 can further include a first decision (Block 95) in which the data from the verification procedure 94 is analyzed to determine whether the treatment is complete. If the treatment is not complete, the method 90 further includes a second decision (Block 96) in which the results of the verification procedure are analyzed to determine whether the treatment plan should be revised to compensate for changes in the target. If revisions are necessary, the method can proceed with repeating the planning procedure 91. On the other hand, if the treatment plan is providing adequate results, the method 90 can proceed by repeating the setup procedure 92, radiation session 93, and verification procedure 94 in a subsequent fraction of the radiation therapy.

The localization system 10 provides several features, either individually or in combination with each other, that enhance the ability to accurately deliver high doses of radiation to targets within tight margins. For example, many embodiments of the localization system use leadless markers that are substantially fixed with respect to the target. The markers accordingly move either directly with the target or in a relationship proportional to the movement of the target. Moreover, many aspects of the localization system 10 use a non-ionizing energy to track the leadless markers in an external, absolute reference frame in a manner that provides objective output. In general, the objective output is determined in a computer system without having a human interpret data (e.g., images) while the localization system 10 tracks the target and provides the objective output. This significantly reduces the latency between the time when the position of the marker is sensed and the objective output is provided to a device or a user. For example, this enables an objective output responsive to the location of the target to be provided at least substantially contemporaneously with collecting the position data of the marker. The system also effectively eliminates inter-user variability associated with subjective interpretation of data (e.g., images).

F. Embodiments of Anchorable Markers

Figure 13:
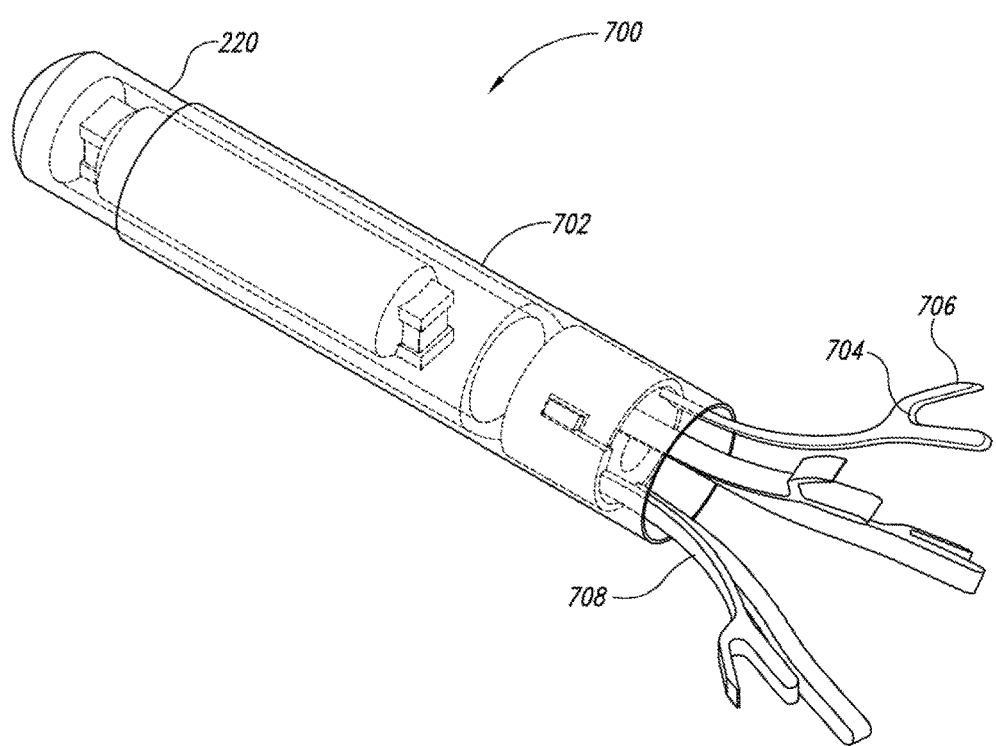
FIG. 13 is an isometric view of an anchorable marker assembly configured in accordance with an embodiment of the present technology.

Referring now to FIG. 13, an anchorable marker assembly includes a marker 220 having a casing, a magnetic transponder (e.g., a resonating circuit) at least partially encased in the casing, a shell assembly 702 and an anchor assembly. The anchor assembly includes an anchor disk 710 (shown in later figures) and fasteners 708 such as shape memory legs, extending from the anchor disk 712.

Figure 14A:
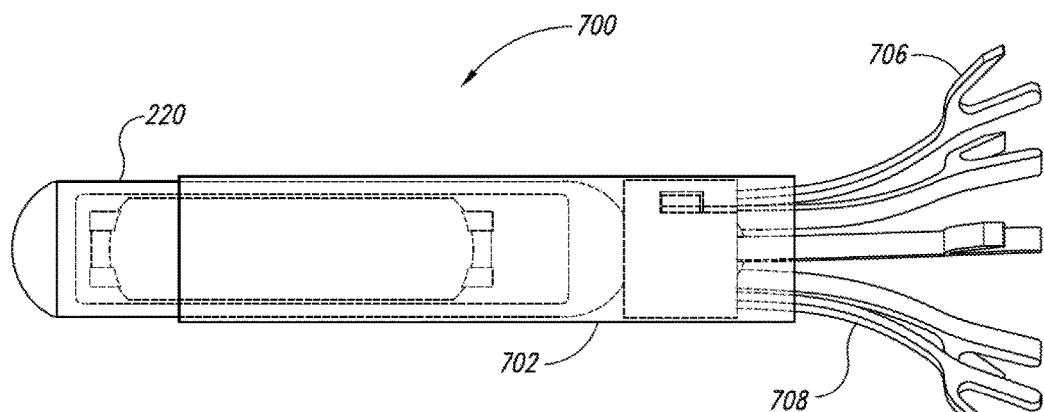
FIGS. 14A and 14B are a side view and a partial cut-away isometric view, respectively, of an anchorable marker assembly configured in accordance with an embodiment of the present technology.
Figure 14B:
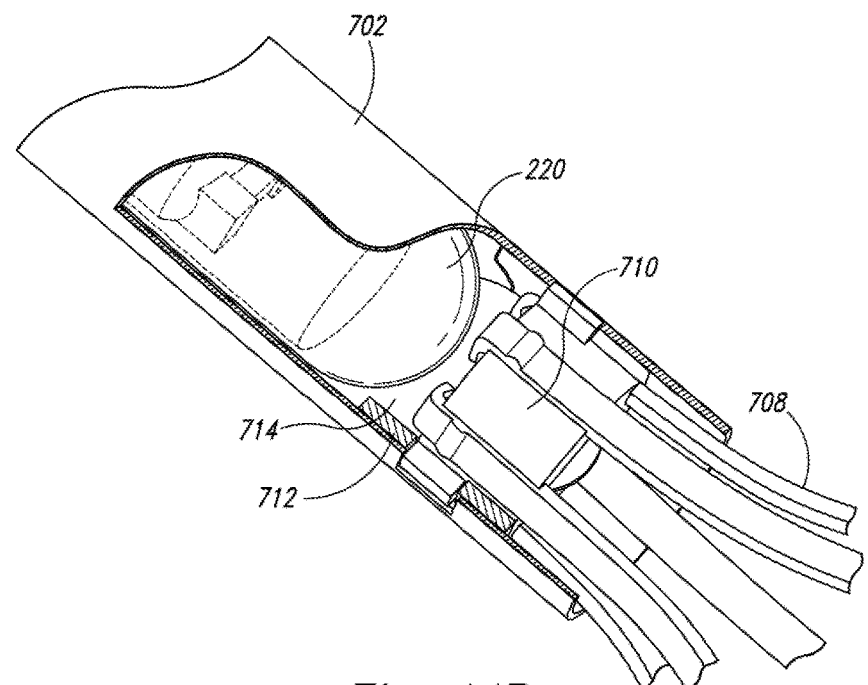

Referring now to FIGS. 14A and 14B, an anchorable marker assembly 700 may include a marker 220, a shell assembly 702 around the marker 220, an anchor disk 710 adjacent to a proximal end of the marker 220, and a plurality of fasteners or legs 708 attaching to the anchor disk 710 and extending proximally. The legs 708 may further include an end stop 704 at a far proximal end. The end stop 704 may further include a barb 706 extending at an angle outward. As further shown in the cutaway view of FIG. 14B, the anchor disk 710 may be held in a fixed position in the shell assembly 702 by anchor sleeve 712 and adhesive 714.

Figure 15:
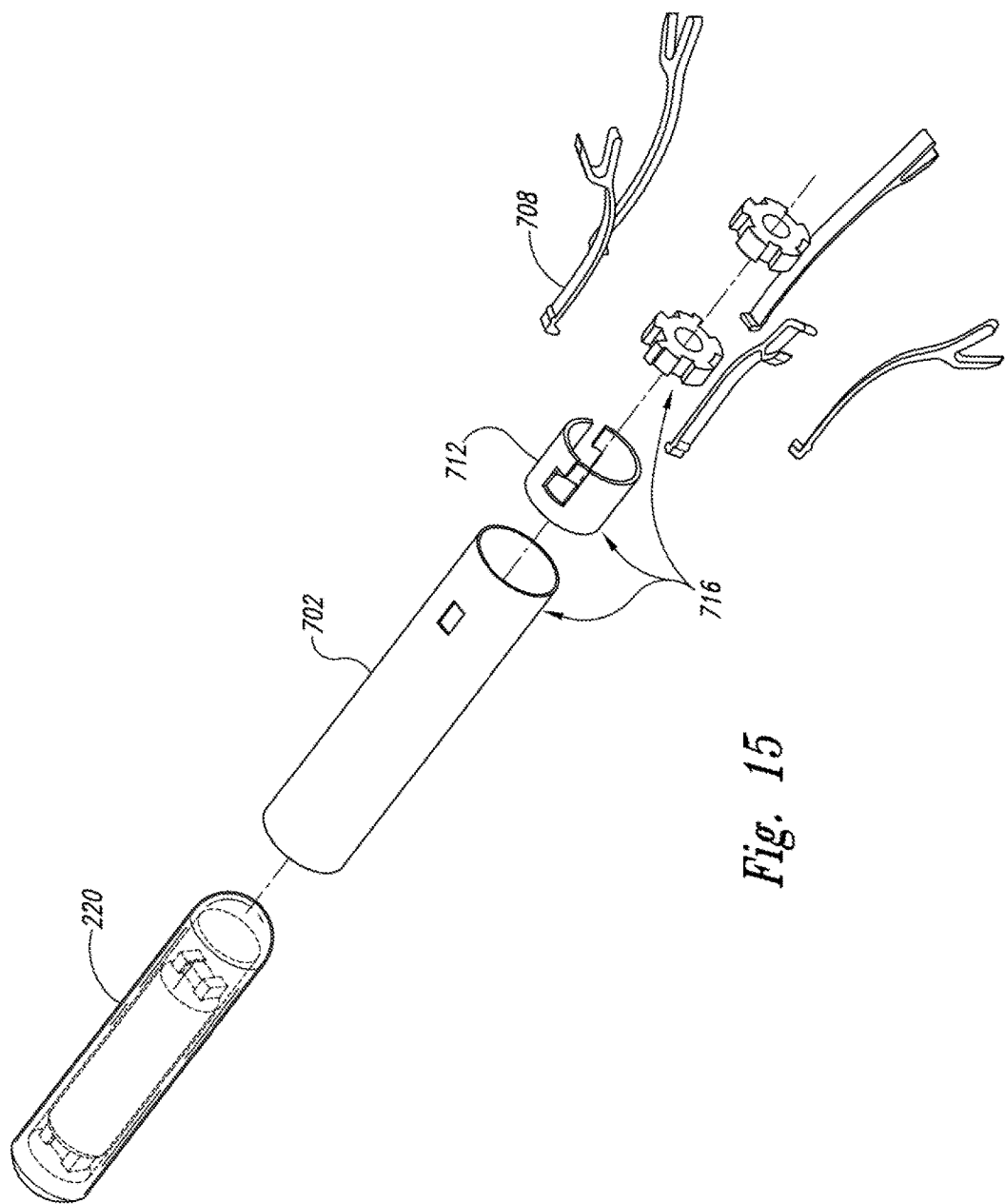
FIG. 15 is an exploded isometric view of the anchorable marker assembly of FIGS. 14A and 14B.

Referring now to FIG. 15, an exploded view of the anchorable assembly 700 of FIGS. 14A and 14B is shown. According to this embodiment, the shell assembly 702, the anchor sleeve 712, the legs 708 and the anchor disk may interlock 716 during assembly. This mechanical interlock between the shell components and the Nitinol® leg stability feature provides a high intra-component mechanical strength. According to alternative embodiments, the legs may be mated into grooves in the anchor disk, providing further positive mechanical interlock. Other interlock configurations may be used within the scope of this disclosure, including but not limited to: star shaped and inverted star shape anchor disk; direct leg-to-shell interlock; single piece multi-leg cage interlocks and the like.

Figure 16A:
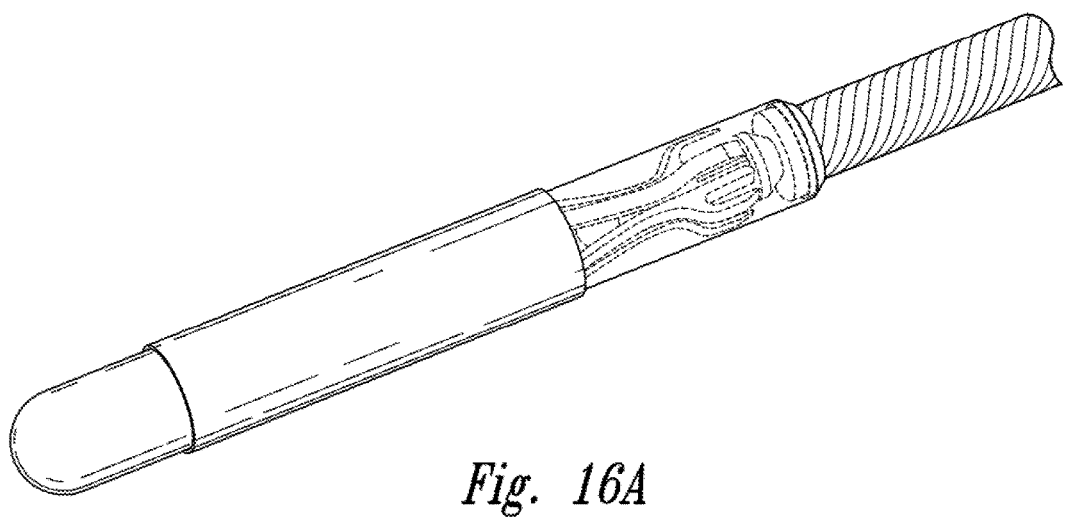
FIGS. 16A-16C are isometric views of a delivery catheter with a pre-loaded anchorable marker assembly in a loaded state (FIGS. 16A and 16*b*) and a deployed state (FIG. 16C) in accordance with an embodiment of the present technology.
Figure 16B:
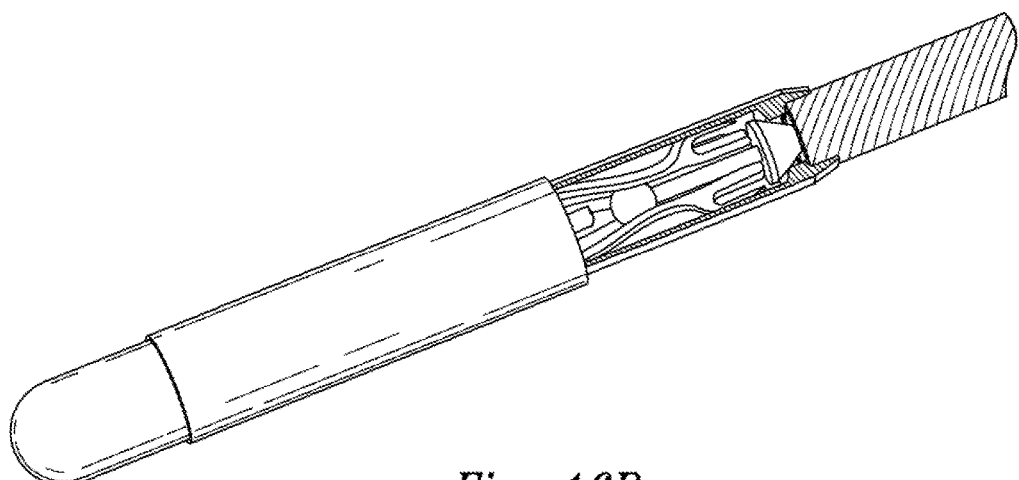
Figure 16C:
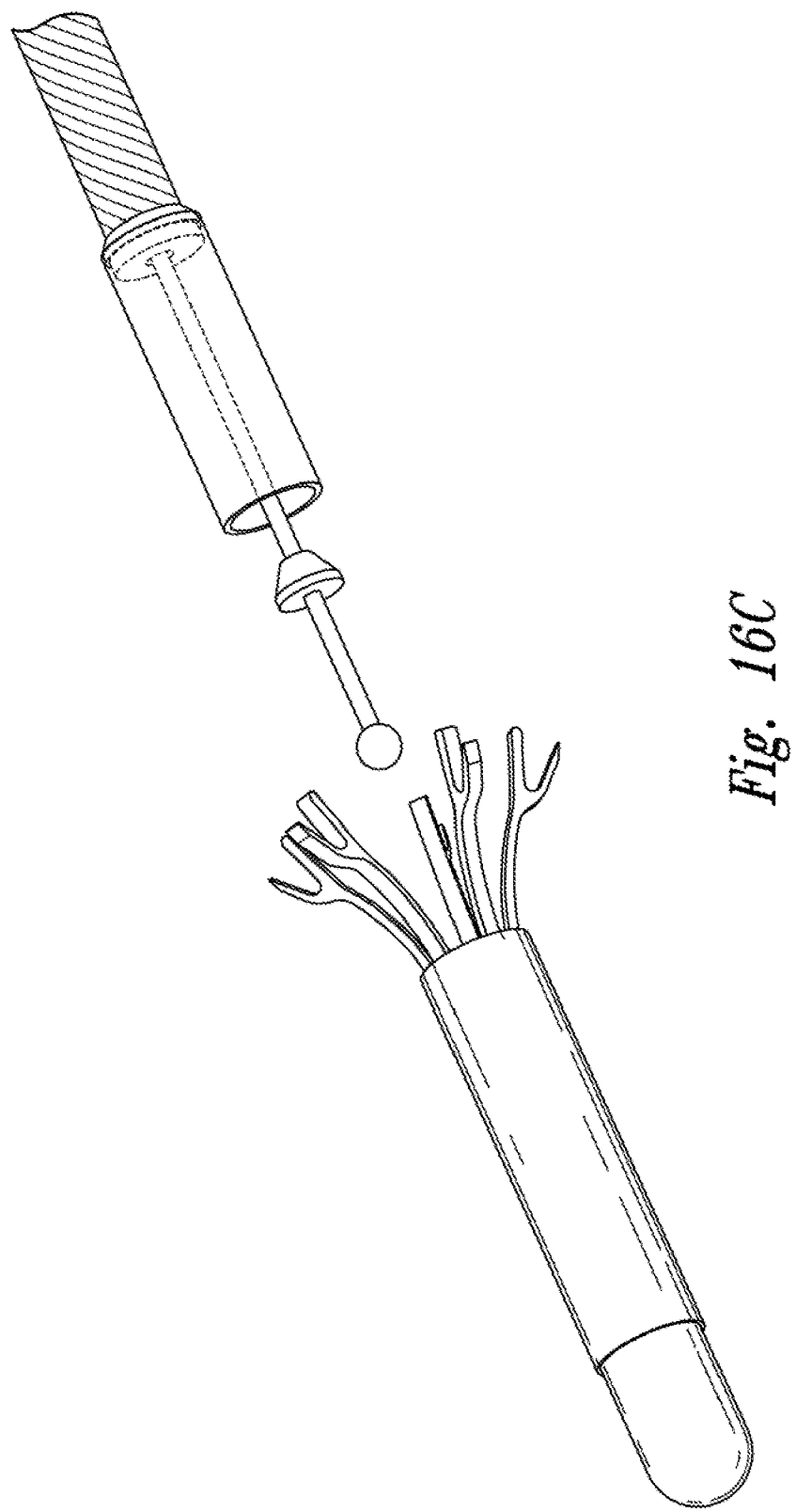

Referring now to FIGS. 16A, 16B and 16C a delivery catheter with a pre-loaded anchorable marker assembly, including the loaded catheter assembly of FIG. 16A, is shown. FIG. 16B shows a cutaway view of the loaded catheter and FIG. 16C shows a deployed view of the marker after it has been deployed from the catheter. As illustrated in this embodiment, the internal shell-catheter may overlap for articulation in use. The exemplary configuration allows the distal end of the catheter to dock with the marker and articulation between the marker and the catheter provides axial flexibility and a reduction in forces when passing through tortuous or curved pathways. Furthermore, an internal shell-catheter overlap may cover a sharp edge on the deliver catheter to avoid airway wall injury.

Figure 17A:
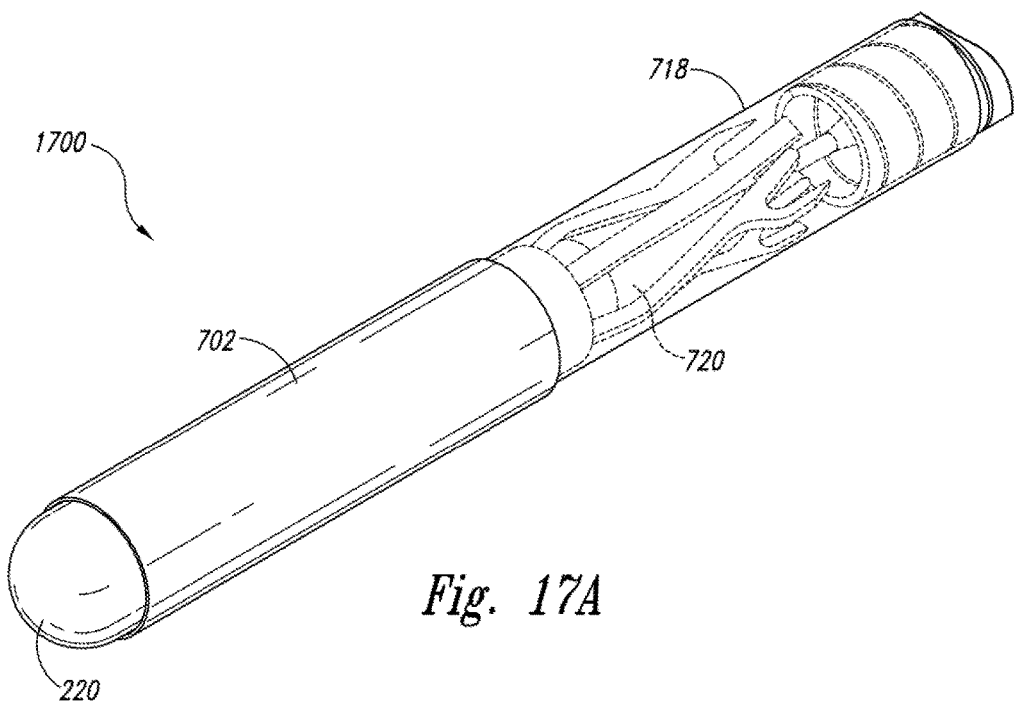
FIGS. 17A and 17B are isometric views of a delivery catheter with a pre-loaded anchorable marker assembly in a loaded state and a deployed state, respectively, in accordance with another embodiment of the present technology.
Figure 17B:
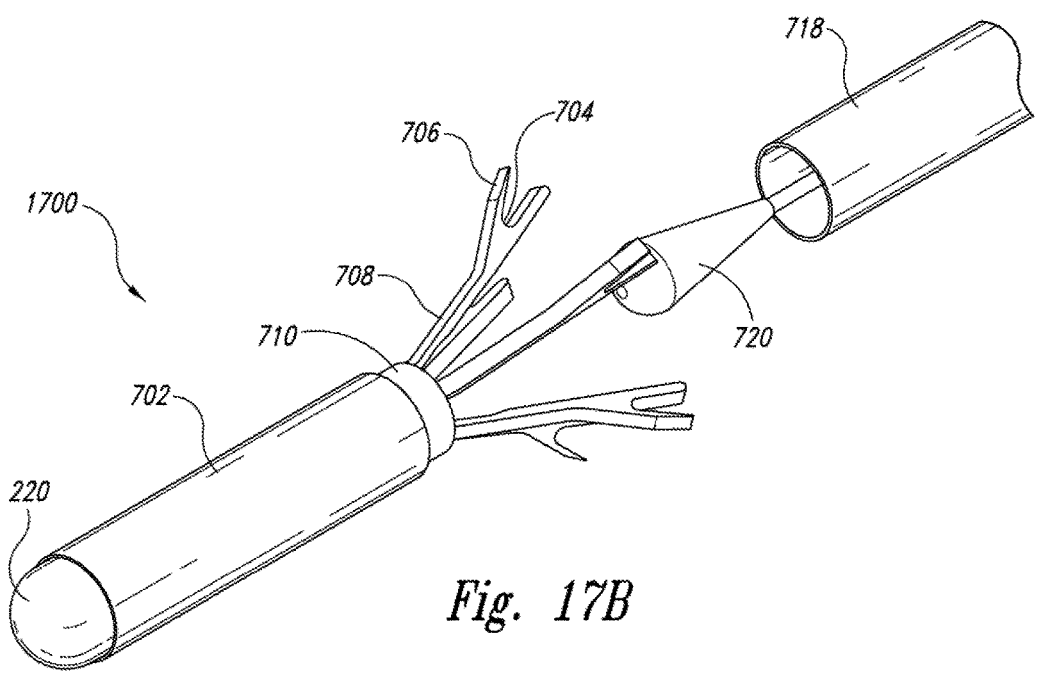

Referring now to FIGS. 17A and 17B, a preloaded delivery catheter 1700 and an anchorable marker assembly deployed from the delivery catheter are shown. According to this embodiment, the distal end of the push wire includes an engagement member 720. In this embodiment, the engagement member is configured as a retention bulb shaped to retain the fasteners 708 when the anchorable marker assembly is retained in the delivery catheter prior to deployment. As will be appreciated by one skilled in the art, the engagement member may take any geometrical shape to nest within and retain the fasteners when the anchorable marker assembly is retained in the delivery catheter prior to deployment.

Figure 18A:
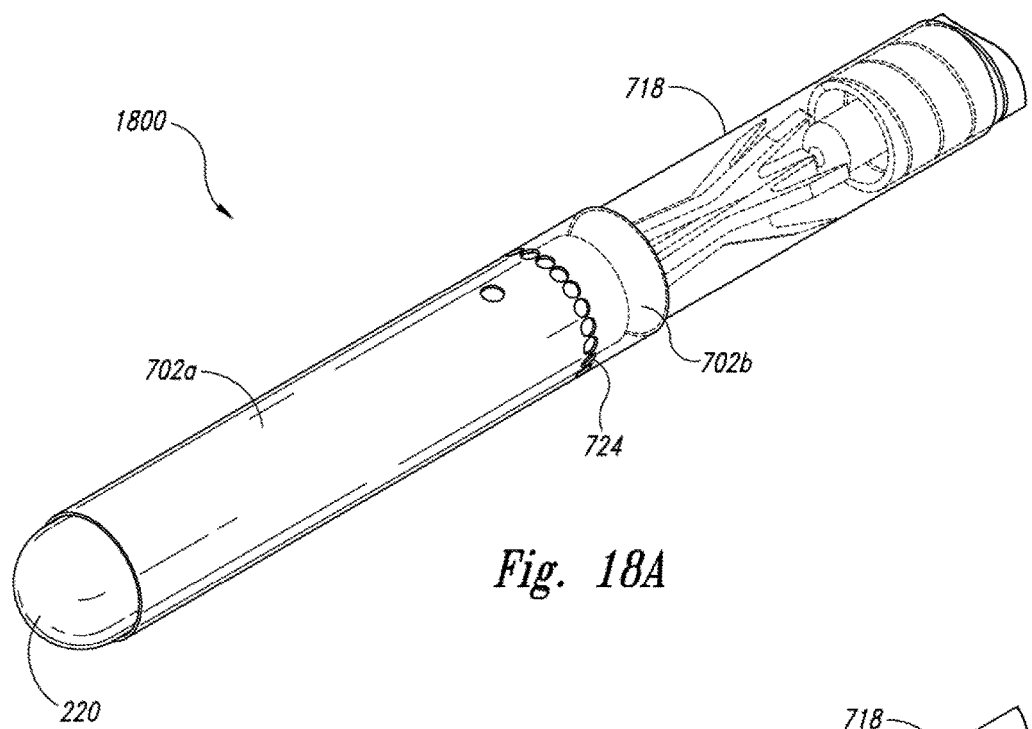
FIGS. 18A and 18B are isometric views of a delivery catheter with a pre-loaded anchorable marker assembly in a loaded state and a deployed state, respectively, in accordance with yet another embodiment of the present technology.
Figure 18B:
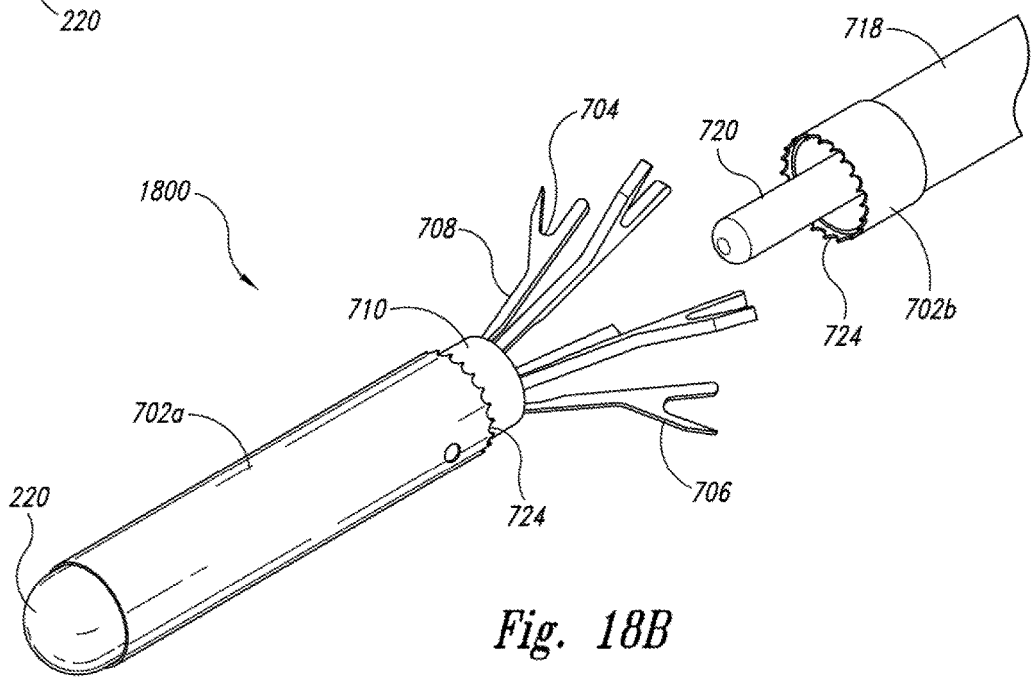

FIG. 18A shows a preloaded delivery catheter 1800 and FIG. 18B shows an anchorable marker assembly after being deployed from the delivery catheter. According to this embodiment, the distal end of the push wire includes an engagement member 720. According to further aspects, a breakaway means is included between a first part 702*a* of the shell assembly 702 and a second part 702*b* of the shell assembly 702. In operation, the marker is deployed when the deployment force exceeds a breakaway force. The breakaway means may include a weakened portion of the shell assembly 702 in the form of a perforation, crease, thinned section or the like. According to alternative embodiments, a local deformation or crumple zone may exist to accommodate permanent deformation in the shell. The deformation zone can be designed to allow deformation in a specific region (e.g. between the first part 702*a* of the shell assembly 702 and the second part 702*b* of the shell assembly) without damage to function and performance of the shell assembly 702.

Figure 19A:
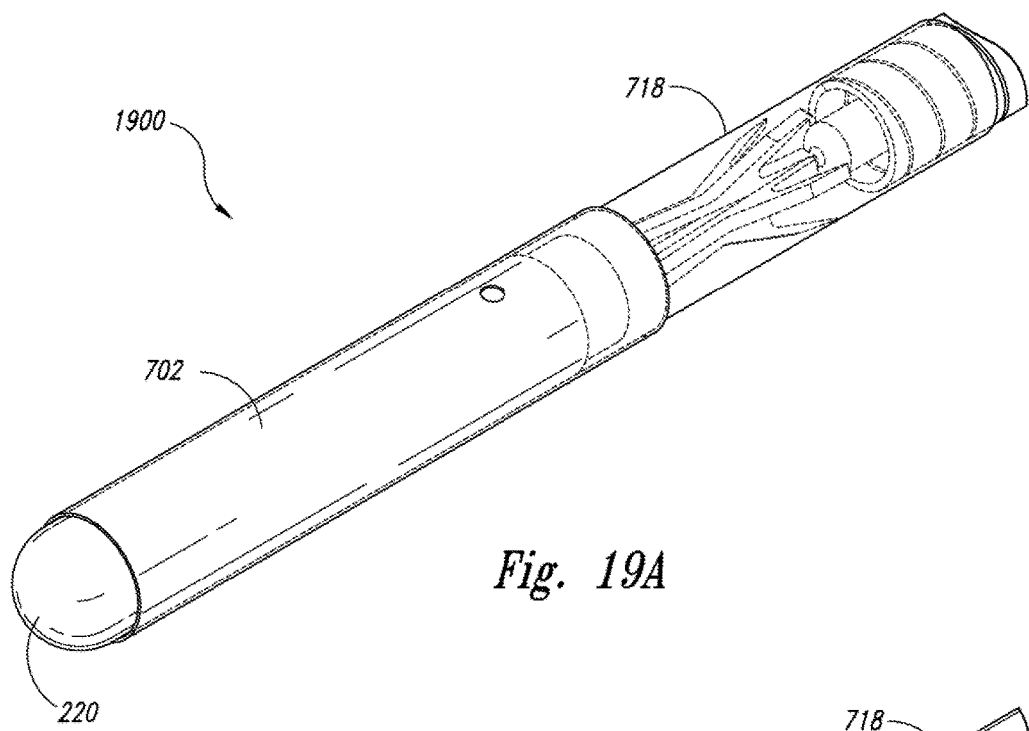
FIGS. 19A and 19B are isometric views of a delivery catheter with a pre-loaded anchorable marker assembly in a loaded state and a deployed state, respectively, in accordance with a further embodiment of the present technology.
Figure 19B:
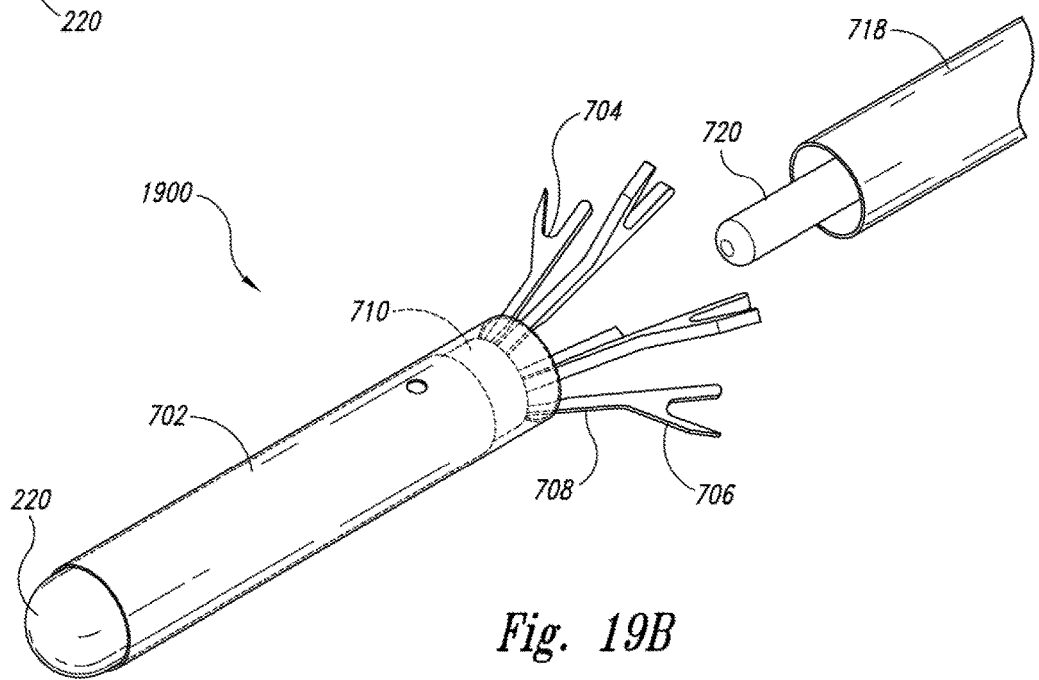

Referring now to FIGS. 19A and 19B, a preloaded delivery catheter 1900 and an anchorable marker assembly deployed from the delivery catheter is shown. According to this embodiment, the distal end of the push wire includes an engagement member 720. In this embodiment, the shell assembly 702 extends proximally over the anchor disk 710 and over some portion of the fasteners 704 to form a skirt at the proximal end of the marker. According to aspects of this embodiment, the overlap at the marker/catheter interface ensures that the marker and the catheter remain engaged during handling of preloaded catheters and while passing the preloaded catheter through small bend radii. According to still further aspects, the overlap provides a flexibility at the marker/catheter interface and can further include an articulated section at the marker/catheter interface.

Figure 20A:
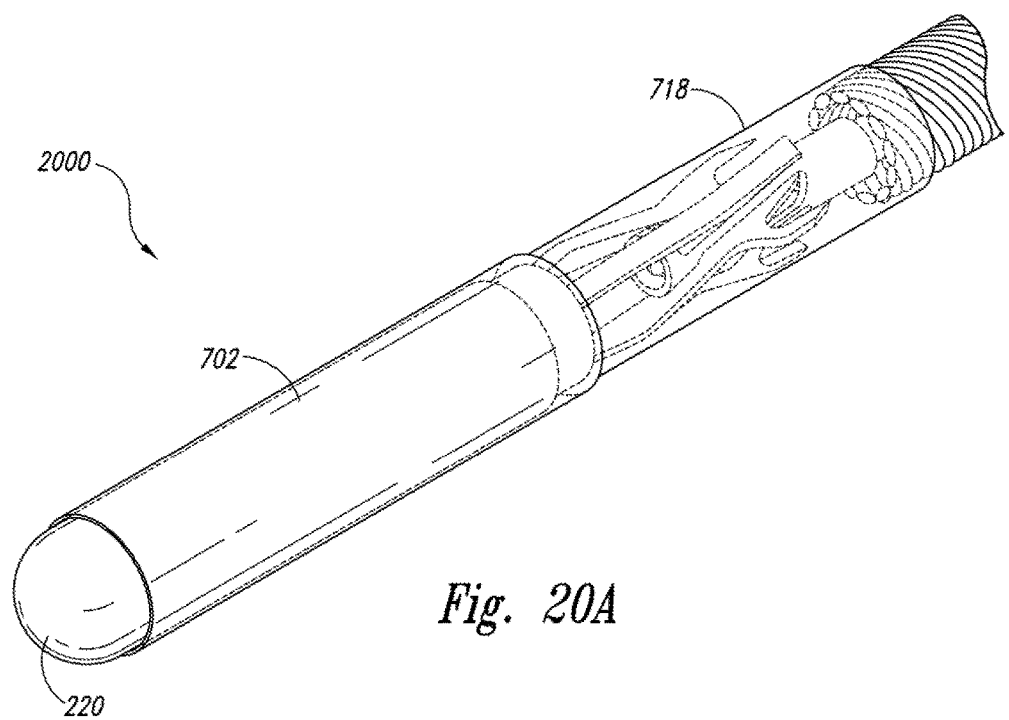
FIGS. 20A and 20B are isometric views of a delivery catheter with a pre-loaded anchorable marker assembly in a loaded state and a deployed state, respectively, in accordance with an additional embodiment of the present technology.
Figure 20B:
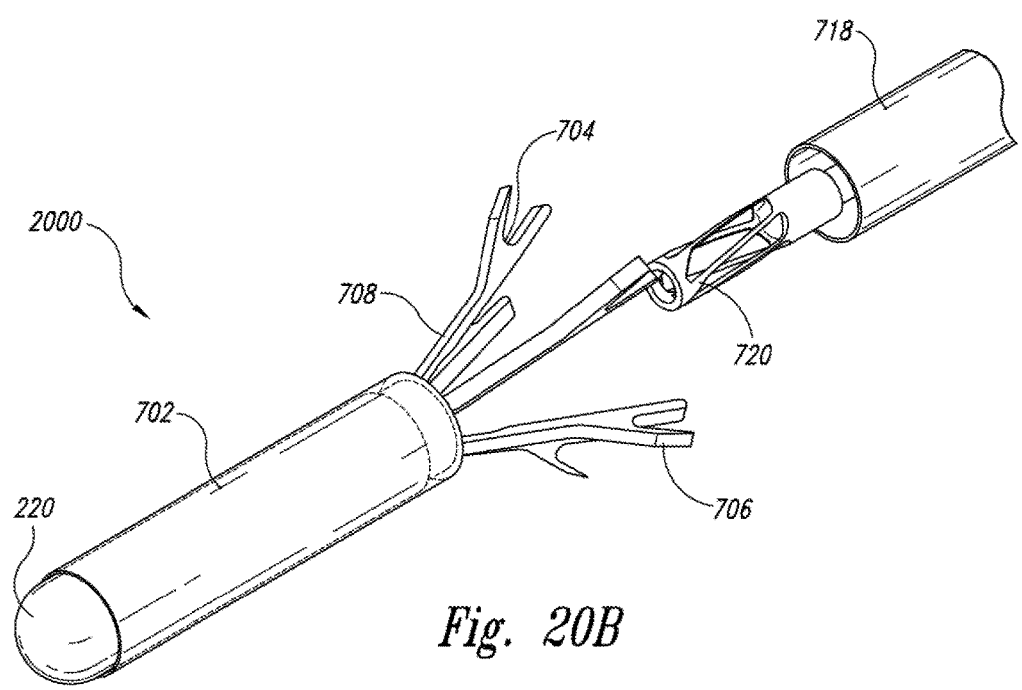

FIG. 20A shows a preloaded delivery catheter 2000 and Figure B shows an anchorable marker assembly deployed from the delivery catheter. According to this embodiment, the distal end of the push wire includes an engagement member 720. In this embodiment, the engagement member is configured as an interlock having recesses shaped to engage the fasteners 708 when the anchorable marker assembly is retained in the delivery catheter prior to deployment. According to aspects of this embodiment, the interlocking engagement member provides a positive mechanical interlock to retain the marker in the preloaded catheter.

Figure 21A:
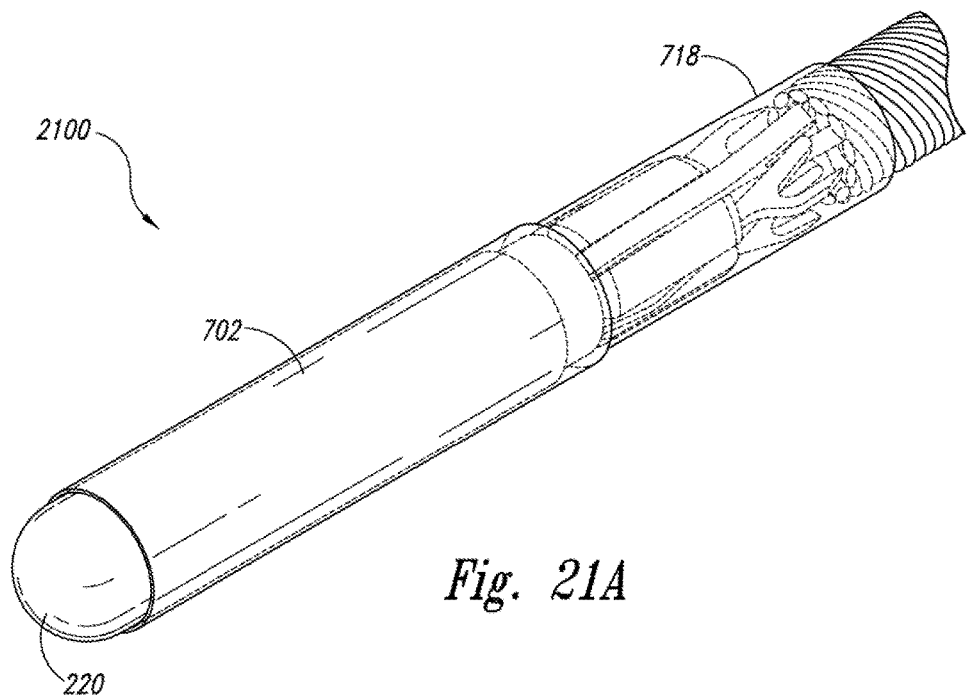
FIGS. 21A and 21B are isometric views of a delivery catheter with a pre-loaded anchorable marker assembly in a loaded state and a deployed state, respectively, in accordance with yet another embodiment of the present technology.
Figure 21B:
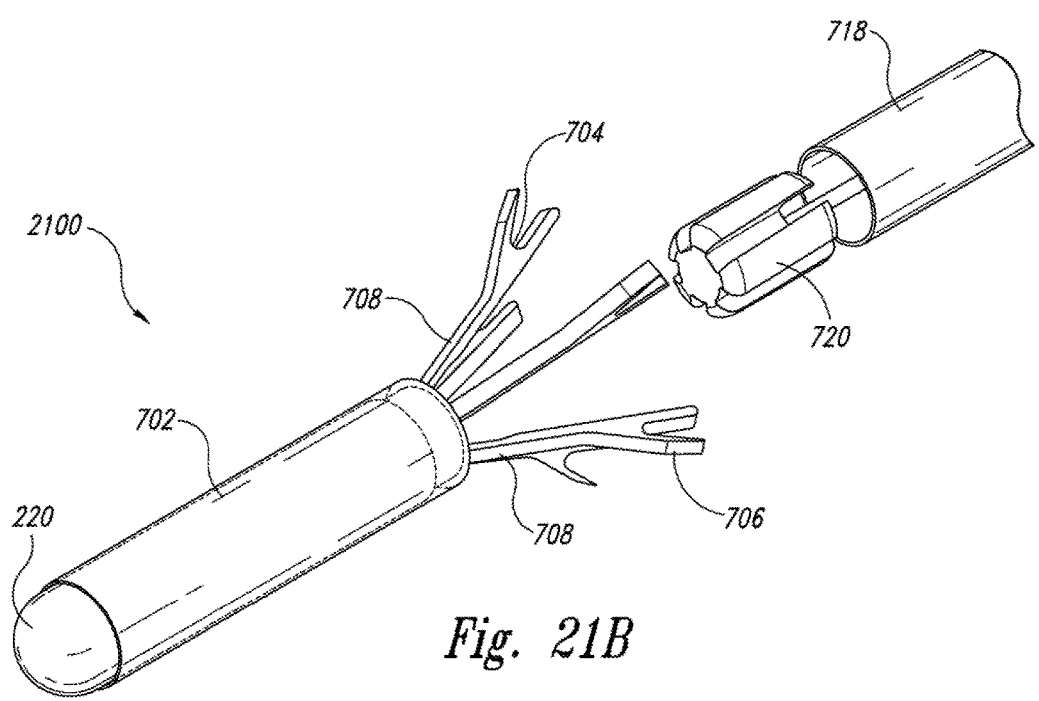

FIG. 21A shows a preloaded delivery catheter 2100 and FIG. 21B shows an anchorable marker assembly deployed from the delivery catheter. According to this embodiment, the distal end of the push wire includes an engagement member 720. In this embodiment, the engagement member is configured as a further interlock shape configured to include slots to receive the fasteners 708 when the anchorable marker assembly is retained in the delivery catheter prior to deployment. In this embodiment, the engagement member is configured as an interlock shaped to engage the fasteners 708 when the anchorable marker assembly is retained in the delivery catheter prior to deployment. According to aspects of this embodiment, the interlocking engagement member provides more positive mechanical interlock to retain the maker in the preloaded catheter.

Figure 22A:
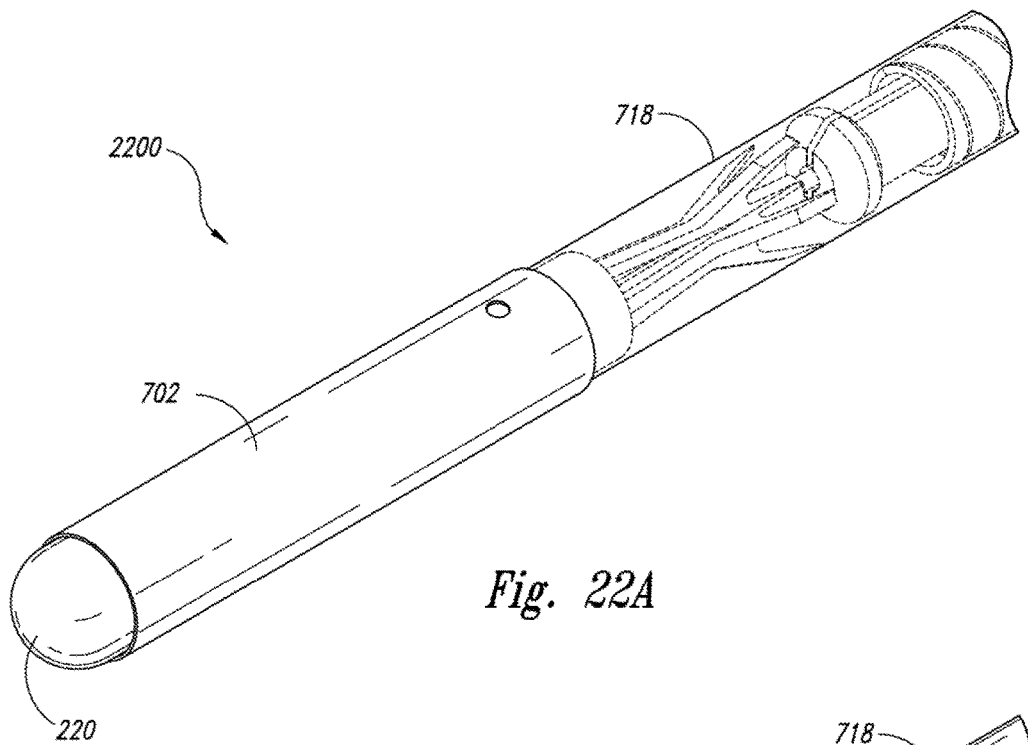
FIGS. 22A and 22B are isometric views of a delivery catheter with a pre-loaded anchorable marker assembly in a loaded state and a deployed state, respectively, in accordance with still another embodiment of the present technology.
Figure 22B:
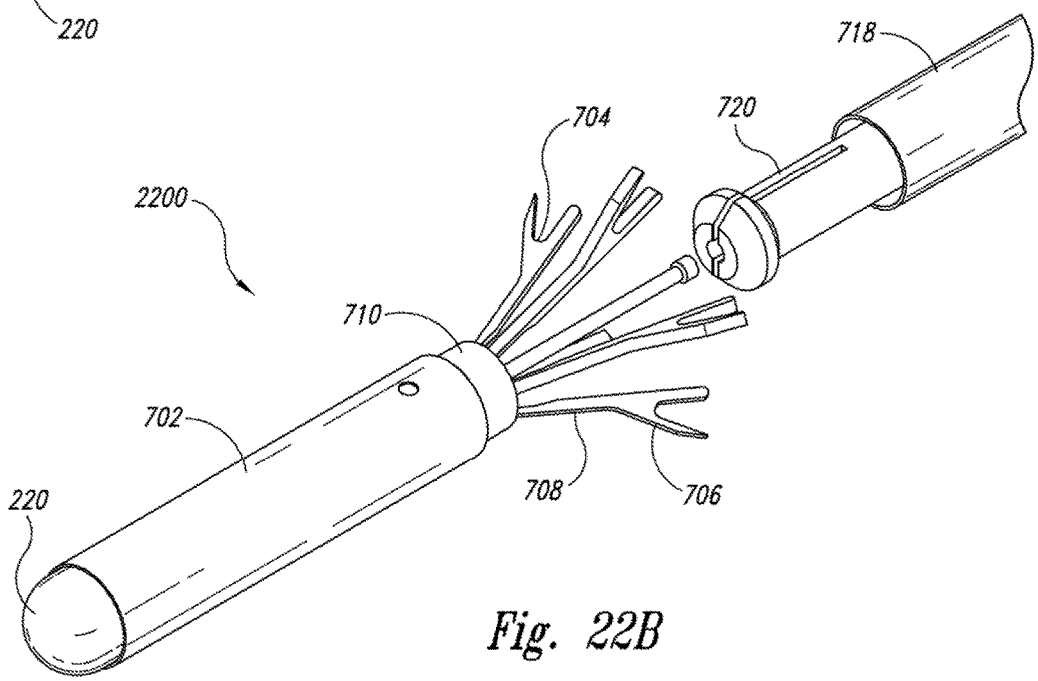

FIG. 22A shows a preloaded delivery catheter 2200 and FIG. 22B shows an anchorable marker assembly deployed from the delivery catheter. According to this embodiment, the distal end of the push wire includes an engagement member 720. In this embodiment, the engagement member is configured as a retention bulb which includes a collet for receiving an element of the fastener assembly shown in this embodiment to include a larger diameter head at a distal end for engaging the engagement member. The engagement member is configured to receive the element 707*a* of the fastener assembly in the collet to provide a positive mechanical interlock to retain the anchorable marker assembly in the delivery catheter prior to deployment.

Figure 23A:
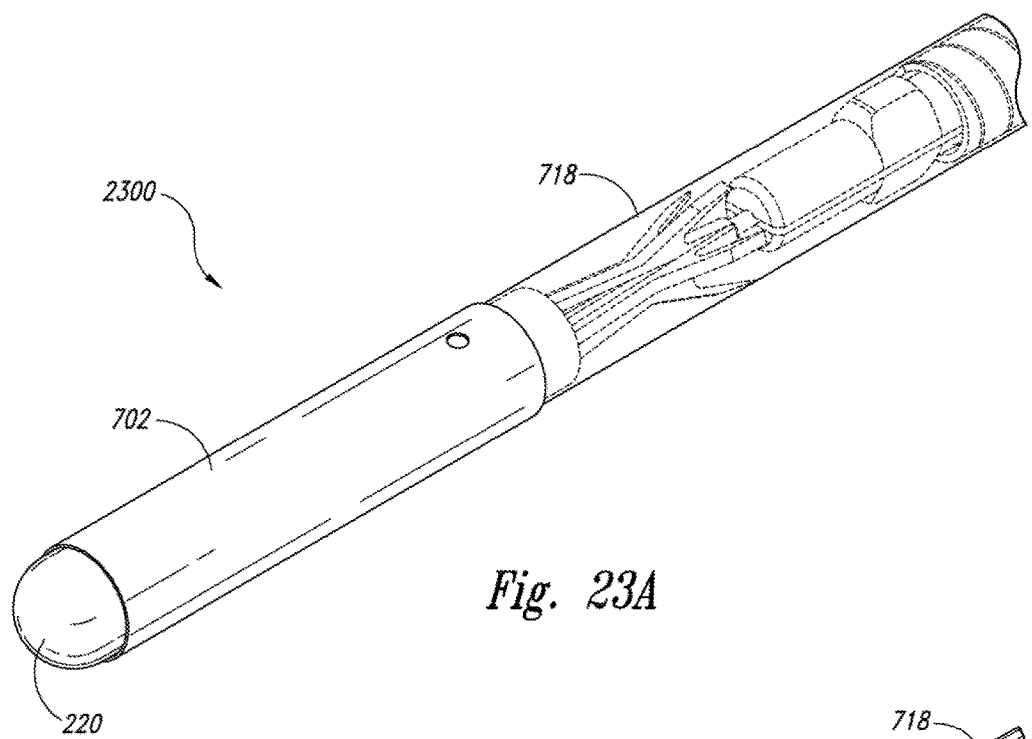
FIGS. 23A and 23B are isometric views of a delivery catheter with a pre-loaded anchorable marker assembly in a loaded state and a deployed state, respectively, in accordance with an additional embodiment of the present technology.
Figure 23B:
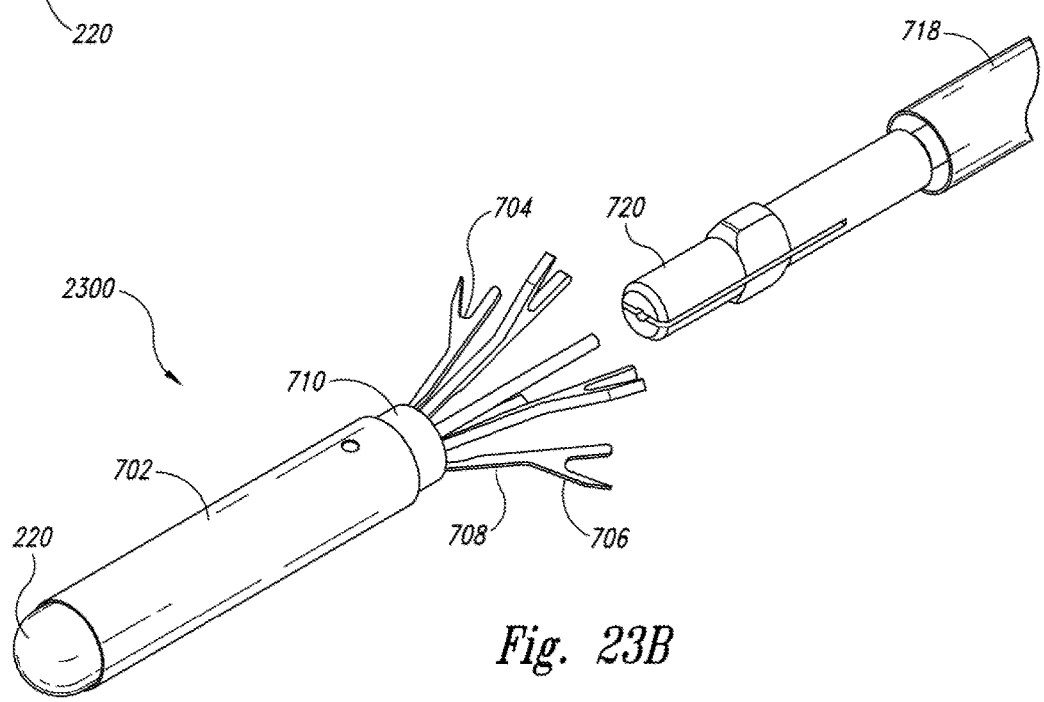

FIG. 23A shows a preloaded delivery catheter 2300 and FIG. 23B shows an anchorable marker assembly deployed from the delivery catheter. In alternative embodiments, the marker is not preloaded in the delivery catheter. According to this embodiment, the distal end of the push wire includes an engagement member 720. In this embodiment, the engagement member is configured as a retention rod which includes a collet for receiving an element 707*b* of the fastener assembly. The engagement member is configured to receive the retained member 707*b* in the collet to provide a positive mechanical interlock to retain the anchorable marker assembly in the delivery catheter prior to deployment.

Figure 24A:
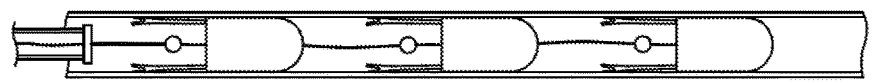
FIGS. 24A-24D are cross-sectional and end views of anchorable assemblies having various loading and unloading configurations in accordance with embodiments of the present technology.
Figure 24B:
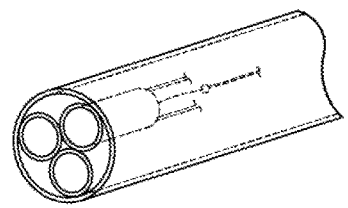
Figure 24C:
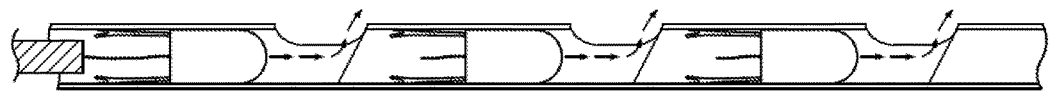
Figure 24D:
Figure 26:
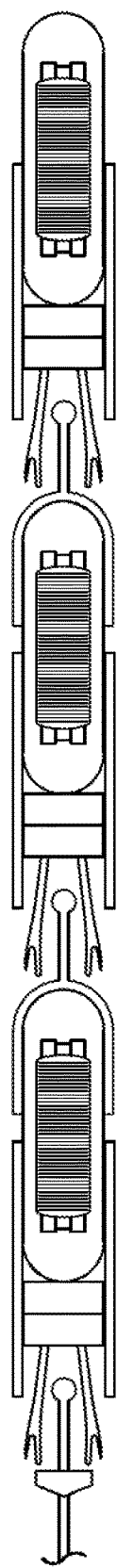
FIG. 26 is a side view of multiple anchorable marker assemblies in an interconnected configuration configured in accordance with an embodiment of the present technology.

Referring now to FIGS. 24A-24D, cross-sectional and end views of the anchorable assemblies illustrating various loading and unloading configurations are shown. For example in FIG. 24A, anchorable marker assemblies are shown loaded in the deliver catheter in series. An alternate loading configuration shown in FIG. 24B shows the anchorable assemblies loaded in parallel in a delivery catheter. One skilled in the art will understand that a variety of single and multiple loading configurations are within the disclosure of this application. Referring now to FIG. 24C, an alternative unloading pattern is illustrated wherein the markers are directed to exit the delivery catheter out a side portal of the catheter. According to the embodiment shown in FIG. 24D, multiple individual anchorable marker assemblies are loaded in an untethered manner, separated by a dimple on the interior surface of the delivery catheter. As will be understood by one skilled in the art, separation means may include a mechanical plug, ridge, bladder or other separation device, or may include a spacer of fluid, paste, gel or the like. Referring now to FIG. 26, multiple anchorable marker assemblies may alternatively be deployed from an interconnected configuration wherein the anti-migration element on a first marker engages with a retaining element on a second marker.

Figure 25A:
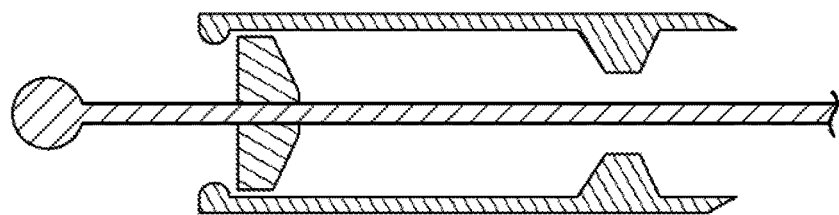
FIGS. 25A-25D are cross-sectional views illustrating various positive stops that provide controlled deployment in accordance with embodiments of the present technology.
Figure 25B:
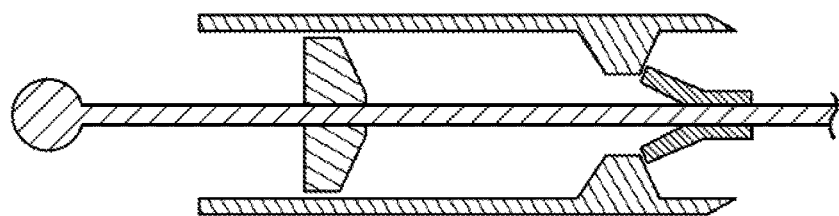
Figure 25C:
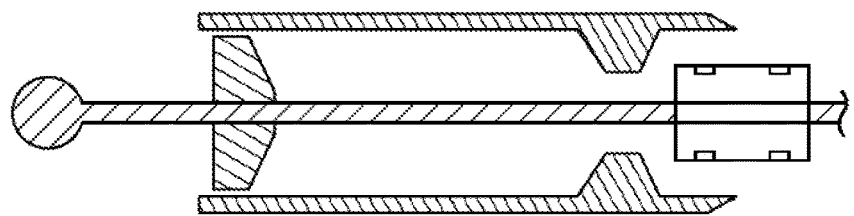
Figure 25D:
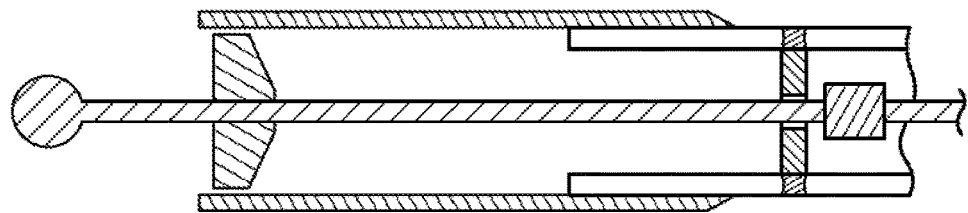

Referring now to FIGS. 25A-25D, various positive stops are illustrated which provide controlled deployment stroke upon implementation. Referring to FIG. 25A, a dimple at a distal end of the delivery catheter may engage with a collar portion of the push wire to provide a first stop for preventing the user from over-deploying. Also shown in FIG. 25A is a protrusion extending from an interior of the catheter configured to engage the collar portion of the push wire and provide a second stop configured to prevent over retraction of the push wire. Referring to FIG. 25B, two stops may be provided, however in this embodiment, both engage with a common protrusion shown on an interior of the catheter. According to this embodiment, a first stop prevents the user from retracting the push wire beyond a predetermined distance and a second stop prevents the user from over inserting the push wire beyond a predetermined distance. Referring to FIGS. 25C and 25D, alternative deployment stop configurations are shown. It is recognized by those skilled in the art that alternative stops beyond the representative stops shown in FIGS. 25A-25D may be included and still fall within the scope of the disclosure. Furthermore, in operation, the distal end stop can provide implant placement accuracy to less than 5 mm, by controlling the stroke required to deploy the implant from the retention sleeve. Additionally, the distal end stop can limit ball protrusion from the retention sleeve; hold the deployment wire centered with respect to the retention sleeve during loading; prevent the legs from becoming entrapped behind disk after deployment; and minimize the likelihood of implant legs catching on ball during retraction.

According to further aspects of the disclosure, the casing is a biocompatible barrier, which can be made from plastics, ceramics, glass or other suitable materials, and the casing is configured to be implanted in the patient. The casing can be a generally cylindrical capsule that is sized to fit within a catheter for bronchoscopic implantation. For example, the casing can have a diameter of approximately 2 mm or less. According to aspects of the invention, the casing can have a slightly larger diameter than the inside diameter of the delivery catheter to retain the casing in the catheter during placement.

According to still further aspects of the disclosure, the magnetic transponder can include a resonating circuit that produces a wirelessly transmitted signal in response to a wirelessly transmitted excitation field. In one embodiment, the magnetic transponder comprises a coil defined by a plurality of windings around a conductor. Many embodiments of the magnetic transponder also include a capacitor coupled to the coil. The coil can resonate at a resonant frequency solely using the parasitic capacitance of the windings without having a capacitor, or the resonant frequency can be produced using the combination of the coil and the capacitor. The coil accordingly defines a signal transmitter that generates an alternating magnetic field at the selected resonant frequency in response to the excitation energy either by itself or in combination with the capacitor. The coil generally has 800-2000 turns, and the windings are preferably wound in a tightly layered coil.

The magnetic transponder can further include a core composed of a material having a suitable magnetic permeability. For example, the core can be a ferromagnetic element composed of ferrite or another material. Suitable embodiments of magnetic transponders are disclosed in U.S. patent application Ser. Nos. 10/334,698 and 10/746,888, which are incorporated herein by reference in their entirety.

Several of the embodiments shown in Figures illustrate the anchor may be embedded in the marker or the anchor may be contained in the delivery catheter such that the anchor is deployed adjacent to the marker to prevent the marker from migrating. Alternatively, the fastener can be a separate component attached to and/or embedded in the casing. According to aspects of the invention, a fastener or anchor protruding from the marker casing wherein the fastener can be an integral extension of the casing. When the fastener is a separate component, it can be made from a suitable biocompatible material, such as metals, metal alloys, polymers, PEEK, glass, epoxy adhesive, silicone adhesive and/or other synthetic materials. An example of one such material is spring steel, although other "memory" metal alloys such as Nitinol® may be suitable. According to further aspects of the invention, an outer shape can employ shape memory alloy features that "grow" into bronchiole as internal body temperature expands the alloy.

Another embodiment of a marker comprises a marker section configured to be localized and an anchor attached to the marker section. The anchor comprises an expandable member that moves between a stored position having a first size and a deployed position having a second size greater than the first size. The anchor, for example, can be a stent, an umbrella-like expandable member, or an expandable cylindrical section as shown in the Figures.

Alternative anti-migration devices and methods that prevent the transponder from moving from the implantation position to a more proximal position relative to the trachea include positioning the anti-migration device either behind the transponder in the catheter or delivered through the catheter after transponder deployment (e.g., glue). Additionally, glue or other chemical material may be delivered through the delivery catheter to function as an anti-migration device. The glue may be pre-packaged within the catheter or injected through the catheter after implantation. Alternatively, a hydroscopic material that expands due to contact with bodily fluids may act as an anti-migration device, for example, a hydrogel, a hygroscopic material, and/or a sponge. According to yet another embodiment, suture material may be pushed out of the catheter and compacted to plug the vessel and serve as an anti-migration device.

Alternative design of the anti-migration devices such as: legs without barbs; barbs contained on some of the legs but not others; a plurality of legs with unequal leg length; a braided stability feature; a coil stability feature, long length leg stability feature design; coils; interconnected legs and/or spring loaded stability features are all within the scope of the disclosure as will be understood by one skilled in the art.

G. Alternative Embodiments of Anchorable Markers

According to alternative aspects of the disclosure, the design allows for the ability to retrieve the implant from airway after implantation. During a bronchoscopic procedure, a commercially available accessory tool (eg. biopsy forceps, snare, retrieval basket) is used to grasp a single leg or multiple legs of the stability feature and retrieve from the airway.

Further in accordance with the disclosure, bronchoscopic implantation of an implant in the airway has a lower risk of complication when compared to a needle based percutaneous implantation in the airway, and therefore bronchscopic placement is the preferred method.

An alternative embodiment provides for central airway application, wherein the implant is implanted in a larger diameter airway. Design changes to the implant are expected to focus on a scale-up of the stability feature, designed for positional stability in larger airways, and potentially, allow for retrieval if needed. Alternatively the implant may be implanted in the airway wall; in which case, modification to the stability feature would focus on a scale-down of the stability feature.

According to still further aspects of the disclosure, the catheter delivery device can be include a modified stability feature for implantation in organs, vessels and tissues other than lung airways percutaneously, laparoscopically, natural orifice transluminal endoscopically. Alternatively, the catheter deliver device can include an implant without a stability feature preloaded in a delivery catheter, for example for Catheterization of the Subarachnoid Space and placement in the brain. According to still further embodiments, the stability feature (multi-legged design) could be used to provide positional stability for other devices such as gold seeds, coils, or other fiducial markers implanted in airways in the lung. According to still further embodiments, generic delivery catheter could be used to deliver other devices such as a transponder, gold seeds, coils, or other fiducial markers in the lung. Further in accordance with the disclosure, a delivery catheter design where more than one implant is preloaded in the distal end of the delivery catheter. Such a design would further improve ease of use, and eliminate the workflow due to exchange of the single use catheter after deployment, and introduction of the next delivery catheter.

In operation, once the distal end of the delivery catheter is positioned at the implantation site, the user withdraws the delivery catheter approximately 1-2 cm so as to provide a space for the anchored transponder to be deployed in. This accounts for the travel of the anchored transponder upon handle actuation/deployment, supports accurate placement of the anchored transponder and prevents bronchial injury or serious injury such as pneumothorax. Actuation/deployment can also by accomplished by simultaneous actuation of the handle and withdrawal of the catheter, or actuation/deployment without a space for the anchored transponder to be deployed in.

H. Exemplary Implantation Procedure

In operation, a bronchoscope is inserted into the nose or mouth of a patient past the vocal chords and into the lungs by threading a distal end through the bronchi. At least one marker is pre-loaded at the distal end 216 of the delivery catheter 212. Once the bronchoscope is positioned relative to the tumor or lesion, the delivery catheter 212 is positioned in the working channel of the bronchoscope such that the distal end 216 of the delivery catheter 212 is at or slightly beyond a distal end of the bronchoscope. Once the delivery catheter 212 is in the desired position, the actuator is engaged, causing the push wire to move axially within the channel and deploy the marker. After at least one marker is deployed, a second marker can be deployed; the catheter can be repositioned prior to deploying a second catheter; the catheter can be removed and the bronchoscope can be removed or repositioned to deploy a second marker; or the catheter can be repositioned to deploy a second marker. According to aspect of the invention, as the marker is deployed from the catheter, an anti-migration device integral to the marker or separate from the marker can further be deployed to retain the marker in a desired position. According to this aspect, the anti-migration device anchors the marker to the anatomical anchoring site as further described below.

Anchored transponders should be placed in small airways (approximately 2-2.5 mm in diameter) that are within or near the tumor target to be treated. Preferred placement sites and the bronchoscopic path for reaching them should be determined before beginning the implantation procedure. Anchored transponders may be placed during a standalone procedure or in conjunction with diagnostic bronchoscopy. Implantation should be performed in an ambulatory procedure area or the operating room.

Each anchored transponder includes a small, passive, electrical component encapsulated in biocompatible glass with an affixed multi-legged anchoring feature. The legs of the anchoring feature are constrained in the pre-loaded delivery catheter and become unconstrained, expanding outward, when the anchored transponder is deployed in the airway. According to this embodiment, when completely constrained, the transponder diameter is approximately 2 mm; when the legs are fully expanded, the diameter is approximately 5.5 mm.

Further in accordance with this embodiment, a separate delivery catheter is used to implant each anchored transponder into an airway within or near the treatment target. Each single-use, delivery catheter is pre-loaded with an anchored transponder. According to one embodiment, the distal end of the delivery catheter is approximately 2 mm in diameter. The retention sleeve located at the distal tip of the delivery catheter constrains the legs of the anchored transponder around the deployment wire. According to aspects of one embodiment, the delivery catheter is marked with graduations to assist in monitoring the length of the delivery catheter that has passed through the bronchoscope and into the lung. In this embodiment, the graduations occur every centimeter with a heavier mark every fifth centimeter.

Exemplary Implantation Techniques and Guidelines

Exemplary Guidelines to Provide Positional Stability of the Anchored Transponder when Implanted in an Airway:
  Place the anchored transponders in small airways (approximately 2-2.5 mm in diameter). If an anchored transponder is implanted in a larger airway (diameter>2.5 mm), a greater volume of the lung may be obstructed or the position of the anchored transponder may not be stable.
  For airways within or closely adjacent to a tumor, ensure that the original airway diameter was small (approximately 2-2.5 mm). Airways that have been invaded or compressed by a tumor may expand as a result of therapy induced tumor shrinkage. If the airway expands beyond 2.5 mm, a greater volume of the lung may be obstructed or the positional stability of the implant may be impacted.
  If a central airway contains a stent, make sure that all transponders are implanted beyond the distal end of the airway stent.
  If a sub segmental bronchus contains an airway stent, do not implant an anchored transponder in that airway.
  Do not implant more than one anchored transponder in the same airway.
  Avoid contact with already implanted anchored transponders when implanting subsequent anchored transponders. Plan the order of the implantations such that the anchored transponders in the most distal locations are implanted first.

Guidelines to Ensure an Optimal Configuration of the Anchored Transponders for Use with the Localization and Tracking System
  The anchored transponders can be detectable by a localization system in order to be used for localization and/or tracking. The ability to detect the transponders is influences by their configuration. The following guidelines are provided to help achieve an optimal configuration.
  The anchored transponders should be configured in a triangle and distributed as evenly as possible around the target.
  The distance between anchored transponders is between 1 cm and 7.5 cm.
  Place the anchored transponders in a nonlinear configuration.

Exemplary Anchored Transponder Implantation Procedure
Preparation Before the Implantation Procedure
  1. Determine when to perform the anchored transponder implantation procedure relative to biopsy, chemotherapy, or other events during the patient's course of treatment.
  2. Confirm the patient's eligibility for implantation of the anchored transponders and use of the localization and tracking system.
  3. Using a recent CT scan of the chest as a map of the tracheobronchial tree, determine the intended implantation sites according to the Implantation Site Recommendations. If possible, note the specific airway path leading to each implantation site and the approximate distance the delivery catheter will travel into the airways to reach the intended site.

4. If a dedicated electromagnetic bronchoscopy or other guidance system is used, enter the implantation sites into the system as needed.
5. Per institutional and published guidelines consider antibiotic prophylaxis for bronchoscopic procedures.

Preparation on the Day of Implantation

6. Prepare the patient as you would for a standard bronchoscopy procedure.
7. Per the manufacturer's instructions, prepare any guidance systems (fluoroscopy, electromagnetic guidance, ultrasound, etc.) that you will use for the implantation procedure.
8. Open the package following standard handling procedures and place the delivery catheters on a clean or sterile field per your institution's practices.
9. If you are using a guide catheter, advance the delivery catheter through the guide catheter until the full length of the retention sleeve is outside of the guide catheter. At the proximal end check the graduations to determine the approximate length of the delivery catheter that should protrude from the guide catheter and optionally use a marker to mark the length.

Implantation Procedure

Anchored transponders may be placed during a stand-alone procedure or in conjunction with diagnostic bronchoscopy. Implantation should be performed in an ambulatory procedure area or the operating room. If exploring or confirming navigable airways that lead to the planned implantation site, use of bronchoscopy forceps (in the closed position) or similar accessories is recommended rather than the anchored transponder delivery catheter.

1. Administer sedation or general anesthesia, consistent with your institution's practice for bronchoscopic placement of lung fiducials or other flexible bronchoscopy procedures.
2. Carefully open the pouch on the chevron side, remove the hoop from the pouch and slowly remove the first delivery catheter from its hoop. During handling of the delivery catheter take care not to damage the glass capsule of the transponder located at the distal tip and avoid contact with hard surfaces, and non-clean and/or non-sterile fields.
3. Use a bronchoscope, fluoroscopy and, optionally, a guidance system to advance the delivery catheter to the first implantation site. Begin with the most distal location as recommended in the Implantation Site Recommendations and Implantation Planning section:

When Implanting Directly Through the Instrument Channel of the Bronchoscope Using Fluoroscopic Guidance:

1. Insert the bronchoscope into the lungs and advance it into the airway leading to the first implantation site. At the proximal end of the bronchoscope keep the delivery catheter free of loops and kinks and avoid pinching the catheter where it exits the bronchoscope.
2. In central airways that have an airway stent, maintain the end of the bronchoscope in a position beyond the distal end of the airway stent.
3. Advance the pre-loaded delivery catheter through the bronchoscope's instrument channel until it is visible at the tip of the bronchoscope.
4. Note the position of the tip of the bronchoscope within the tracheobronchial tree and review the previously obtained CT scan to determine the path to follow and the approximate distance from the tip of the bronchoscope to the implantation site.
5. Carefully advance the delivery catheter beyond the tip of the bronchoscope, into the airways leading to the implantation site.
6. Use fluoroscopy to confirm that you are advancing toward the target.
7. Monitor the graduations on the proximal end of the delivery catheter to determine the approximate distance the catheter has advanced into the airways.
8. As needed use fluoroscopy performed from one or more angles to ensure that the delivery catheter tip is not approaching the pleural surface.
9. When fluoroscopy shows that the delivery catheter tip is near the implantation site, monitor the level of resistance felt as you advance the catheter. Resistance will increase when the delivery catheter is in appropriately sized airways about the diameter of the 2 mm tip of the delivery catheter. If needed, retract then advance the delivery catheter to confirm resistance is not due to airway branching. The distal end of the delivery catheter is flexible and will bow when it encounters resistance (the catheter bowing can be monitored by fluoroscopy).
10. If it is necessary to remove the bronchoscope rapidly and unexpectedly while the delivery catheter is in the bronchoscope, remove the delivery catheter from the bronchoscope and check the distal end of the delivery catheter before continuing to use it.

When Implanting Using a Guide Catheter and/or Other Guidance System Beyond the Visual Range of the Bronchoscope:

a) Follow the manufacturer's instructions to place the tip of the guide catheter near the implantation site.
b) Advance the delivery catheter through the guide catheter until the retention sleeve at the tip of the delivery catheter is fully outside of the guide catheter. At the proximal end of the guide catheter keep the delivery catheter free of loops and kinks and avoid pinching the delivery catheter where it exits the guide catheter.
c) The proximal graduations and optional mark made before the implantation procedure can be used to determine the approximate relative advancement of the delivery catheter in the guide sheath.
d) Fluoroscopy may be used to confirm that the retention sleeve is outside of the guide sheath.

1. Using fluoroscopy performed on at least two perpendicular angles, confirm that the distal end of the delivery catheter has reached an acceptable implantation site (see Implant Site Recommendations); optionally, use the radiopaque ruler to estimate that the separations meet the recommendations. If the target is not visible under fluoroscopy monitor other nearby landmarks to determine proximity to the target implantation site.
2. After confirming that the anchored transponder on the distal end of the delivery catheter has reached the implantation site, withdraw the delivery catheter, and guide catheter if being used, approximately 1-2 cm while still monitoring the distal tip under fluoroscopy. Withdrawing the delivery catheter 1-2 cm from the targeted implantation site provides space in the airway for the anchored transponder to be deployed, ensuring correct placement of the anchored transponder and preventing bronchial injury.
3. Release the safety lock on the delivery catheter handle by sliding the lock towards the plunger.
4. While monitoring the deployment under fluoroscopy, deploy the anchored transponder:

a) Consider using cine mode or magnifying the view of the fluoroscopy images during deployment to improve visualization.
b) Actuate the plunger slowly until the anchored transponder legs exit the retention sleeve.
c) Do not simultaneously actuate the plunger and withdraw the bronchoscope or delivery catheter. Simultaneous deployment and withdrawal may result in placing the implant in a more proximal position or larger airway than planned.
d) Stop actuating the plunger when fluoroscopy shows that the anchored transponder has been released from the retention sleeve at the distal end of the delivery catheter (FIG. 9):
5. The legs will expand in the airway indicating that the legs have come into contact with the airway wall.
6. A separation between the distal tip of the retention sleeve and the anchored transponder will be seen.
7. The deployment wire will move independently of the anchored transponder.
   e) Release the pressure on the plunger and confirm under fluoroscopy that the anchored transponder and the delivery catheter are separated. The deployment wire will also retract either partially or fully into the delivery catheter when the pressure is released.
8. While still monitoring under fluoroscopy, begin withdrawing the delivery catheter. Confirm under fluoroscopy that the anchored transponder is fully disengaged from the delivery catheter
9. Withdraw the delivery catheter fully from the bronchoscope.
10. Record the frequency indicator from the delivery catheter (1, 2 or 3) and save or print a fluoroscopic snapshot of the location of the anchored transponder so that the relative geometry of the three frequencies can be recorded after all anchored transponders are implanted.
11. Leave the bronchoscope in place so that the next delivery catheter can be advanced to another implantation site.
12. Dispose of the used delivery catheter in the appropriate biohazard waste container.

Implanting Remaining Anchored Transponders

Repeat the above process to access the next two implantation sites and implant the remaining two anchored transponders. The most distal anchored transponder should have been implanted first. Continue with the next most distal and save the final anchored transponder for the most proximal location.
1. When advancing the delivery catheter to implant the second and third anchored transponders, use fluoroscopy to monitor the proximity of the delivery catheter to the already implanted anchored transponder(s). Take care not to contact the already implanted anchored transponder(s) with the delivery catheter.
2. Ensure the anchored transponders are implanted in a triangle around the tumor target and are at least 1 cm but no more than 7.5 cm from each other; optionally, use the radiopaque ruler to estimate the distance to the tumor target and inter-transponder separations.
3. When all three anchored transponders have been implanted, remove the bronchoscope from the patient.
4. Save or print a posterior-anterior fluoroscopy snapshot showing the three implanted anchored transponders. Annotate each anchored transponder with its frequency indicator (1, 2 or 3) based on the snapshots obtained during implantation. Save or print an additional fluoroscopy snapshot(s) (for example a lateral view) if it will help in identifying the relative geometry of the anchored transponders and their frequencies.
5. Provide the final fluoroscopic view with the annotations to the radiation oncology team.

Mis-Deployed or Dislodged Anchored Transponders

If an anchored transponder is inadvertently mis-deployed or becomes dislodged from its implantation site you may wish to retrieve it or advance it into a small airway.

When to Consider Addressing a Mis-Deployed or Dislodged Anchored Transponder

The following are reasons to consider retrieving an anchored transponder or advancing it into a smaller airway:
1. The mis-deployed anchored transponder is in a larger airway than intended: Anchored transponders should be placed in small airways (approximately 2-2.5 mm in diameter). If an anchored transponder is in a larger airway a higher volume of the lung may be obstructed.
2. The mis-deployed anchored transponder is too far from the tumor target: Anchored transponders should be placed in small airways near the tumor target. If you feel that you can safely advance it closer to the target at the time of implantation without contacting other anchored transponders you may wish to do so.
3. If the radiation oncologist determines that one anchored transponder is too far from the tumor target, the remaining two anchored transponders can still be used for localization.
4. The dislodged anchored transponder is causing clinically relevant symptoms: If at some point throughout the patient's radiation treatment or subsequent follow-up there is concern about clinically relevant symptoms consistent with endobronchial foreign bodies you may wish to address the dislodged anchored transponder.

Conditions for Retrieval

The following are the recommended conditions for retrieval:
1. The anchored transponder can be visualized with the bronchoscope: You must be able to see the anchored transponder using a bronchoscope that has an instrument channel that can accommodate forceps or other foreign body retrieval accessories.
2. The anchored transponder is in a sufficiently large airway: The anchored transponder must be located in an airway that is 5 mm or larger in diameter
3. Three or fewer legs are engaged: The anchored transponder must have three or fewer legs engaged in the airway walls.

When these conditions are met they should minimize the damage to the airways that may occur during retrieval. If the conditions for retrieval are met, review the instructions for retrieval. If the conditions for retrieval are not met, review the conditions and instructions for advancing the anchored transponder into a smaller airway.

Conditions for Advancing into a Smaller Airway
1. If the anchored transponder cannot be retrieved: You may wish to review the conditions for retrieving an anchored transponder and attempt to retrieve it (if the conditions are met) before deciding to advance the anchored transponder into a smaller airway.
2. The advanced anchored transponder should not contact any other anchored transponders: Before advancing an anchored transponder into small diameter airways, you should confirm under fluoroscopy that you will not come into contact with any other anchored transponders when navigating to the anchored transponder or distally advancing it into an airway.

Instructions for Retrieving Anchored Transponders

Anchored transponders should be retrieved using foreign body retrieval techniques and tools consistent with other endobronchial foreign body retrieval. These instructions assume forceps will be used but the instructions are relevant for the use of other retrieval devices or tools (e.g. a foreign body retrieval basket). Mild damage to the airway is possible when retrieving the anchored transponder.

1. Advance the bronchoscope toward the location of the anchored transponder to be retrieved. Position the bronchoscope in close proximity to the anchored transponder. In the case of mis-deployed anchored transponders the bronchoscope will likely already be in an appropriate place for retrieval.
2. Under direct bronchoscopic visualization, advance the forceps through the working channel of the bronchoscope until it is visible beyond the tip of the bronchoscope. Open the forceps and grab one of the five legs of the anchored transponder. It is not necessary to attempt to compress any or all of the legs since retrieval should only be attempted if three or fewer legs have engaged in the airway walls.
3. Once the leg is gripped securely, retract the forceps so that any legs engaged in the airway wall disengage.
4. Once the anchored transponder is free of the airway wall withdraw the forceps until the anchored transponder is near the tip of the scope. Do not allow the anchor legs to contact the end of the bronchoscope to avoid scratching the optical lens at the end of the bronchoscope.
5. Rotate the forceps so that the anchored transponder is oriented with the legs in the shadow of the bronchoscope (all of the legs are seen and the anchored transponder is approximately centered in the field of view of the bronchoscope).
6. Keeping the leg of the anchored transponder gripped by the forceps, retract the bronchoscope and forceps together until all are removed from the patient.
7. While retracting the bronchoscope and forceps monitor the anchored transponder to ensure that the forceps' grip on the anchored transponder is not lost and that the legs do not contact the airway wall.

The localization system can operate with the remaining two anchored transponders after an anchored transponder has been retrieved. The localization plan can be created with two transponders or edited to remove the retrieved transponder from the plan if it already exists (in the case of dislodged anchored transponders).

Instructions for Advancing Anchored Transponders into Small Airways

An anchored transponder can be advanced into small airways when the conditions for anchored transponder retrieval are not met, the anchored transponder cannot be retrieved, or you wish to attempt to place a mis-deployed anchored transponder closer to an implantation site. Mild damage to the airway is possible when advancing the anchored transponder into small airways.

1. Determine what instrument will be used to advance the mis-deployed or dislodged anchored transponder:
    a. If you have mis-deployed the anchored transponder and the tip of the delivery catheter has not been retracted into the bronchoscope you can use the empty delivery catheter to advance the anchored transponder to a smaller airway. If the tip of the delivery catheter has already been retracted into the bronchoscope, do not advance the now-empty delivery catheter through the bronchoscope as it could catch on the inside of the bronchoscope and damage the bronchoscope.
    b. If the tip of the delivery catheter has been retracted into the bronchoscope or if you are managing a dislodged anchored transponder use bronchoscopy forceps or a similar accessory to advance the anchored transponder to a smaller airway.
2. Advance the bronchoscope toward the location of the anchored transponder. Position the bronchoscope in close proximity to the anchored transponder (In the case of mis-deployed anchored transponders the bronchoscope will likely already be in an appropriate position for retrieval.)
3. Advance the delivery catheter or forceps toward the anchored transponder. If you are using forceps, keep the forceps closed.
4. Using the instrument, make contact with the anchored transponder and advance the anchored transponder into a smaller airway.
5. While advancing the anchored transponder use fluoroscopic imaging to monitor the current location and intended final location of the anchored transponder.
6. When advancing anchored transponders distally, avoid using excessive force, contacting other anchored transponders, or approaching the pleural surface.
7. Assess the final location of the mis-deployed or dislodged anchored transponder:
    a. If the final location of the mis-deployed or dislodged anchored transponder does not meet the implantation site recommendations that anchored transponder can be disabled in the patient's localization plan and not used for localization and tracking; the system can operate using the remaining two anchored transponders.
    b. If the final location of the anchored transponder meets the implantation site recommendations, the anchored transponder can be used in the localization plan.

I. Conclusion

From the foregoing, it will be appreciated that specific embodiments of the invention have been described herein for purposes of illustration, but that various modifications may be made without deviating from the spirit and scope of the invention. Accordingly, the invention is not limited except as by the appended claims. The above description of illustrated embodiments, including what is described in the Abstract, is not intended to be exhaustive or to limit the invention to the precise forms disclosed. Although specific embodiments of and examples are described herein for illustrative purposes, various equivalent modifications can be made without departing from the spirit and scope of the invention, as will be recognized by those skilled in the relevant art. The teachings provided herein of the invention can be applied to wireless markers, including gold seeds, not necessarily the exemplary electromagnetic transponders generally described above.

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Unless the context requires otherwise, throughout the specification and claims which follow, the word "comprise" and variations thereof, such as, "comprises" and "comprising" are to be construed in an open, inclusive sense, which is as "including, but not limited to."

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the invention can be modified, if necessary, to employ systems, catheters, markers and concepts of the various patents, applications and publications to provide yet further embodiments of the invention.

These and other changes can be made to the invention in light of the above-detailed description. In general, in the following claims, the terms used should not be construed to limit the invention to the specific embodiments disclosed in the specification and the claims, but should be construed to include all markers that operated in accordance with the claims. Accordingly, the invention is not limited by the disclosure, but instead its scope is to be determined entirely by the following claims.

I claim:

1. A method of deploying and tracking a marker in a body, the method comprising:
   deploying a marker into a lumen within a body, wherein the deploying includes:
      positioning a catheter in the lumen within the body,
      moving a push wire having an integral retention device contained in the catheter toward a distal end of the catheter to engage the integral retention device with fasteners at a first end portion of the marker, wherein the first end portion of the marker is opposite a second end portion of the marker, the second end portion is positioned proximate to a distal terminus of the catheter, and the first end portion is spaced apart from the distal terminus in a proximal direction,
      spring-loading the marker in the catheter while the integral retention device retains the fasteners at the first end of the marker, and
      deploying the marker by moving the push wire toward the distal end of the catheter or by fixing the push wire in place and retracting the catheter toward a proximal end of the push wire;
   determining a fixed relationship between the marker and a treatment target within the body; and
   tracking at least one of position and motion of the marker during treatment.

2. The method of claim 1, wherein positioning includes passing the catheter, push wire, and marker down a working channel of a bronchoscope a selected distance for deployment of the marker into a bronchial lumen of the lung, wherein the working channel of the bronchoscope is lined with polyethylene liner.

3. The method of claim 2 wherein the liner aligns the push wire in a substantial centerline configuration.

4. The method of claim 1 wherein the positioning includes passing the catheter, push wire, and marker down a working channel of a bronchoscope a selected distance for deployment of the marker in a digestive tract lumen.

5. The assembly of claim 1, wherein positioning includes passing the catheter, push wire, and marker down a working channel of a bronchoscope a selected distance for deployment of the marker in a cardiovascular system lumen.

6. The method of claim 1, wherein the marker is a leadless marker having a transponder that has a response signal to an external energy source.

7. The method of claim 1, wherein the marker is radiographically opaque.

8. The method of claim 1, wherein the marker is a radioactive.

9. The method of claim 1, wherein moving the push wire contained in the catheter includes depressing an actuator, and wherein the actuator has indicator marks thereon to indicate when each marker has been deployed.

10. The method of claim 1, further comprising:
    interrupting the treatment when the at least one of the position and the motion of the marker exceeds a predetermined offset value; and
    repositioning the body to bring the at least one of the position and the motion of the marker below the offset value before continuing the treatment.

11. A method of deploying and tracking markers in a patient according to a radiation plan, the method comprising:
    positioning a catheter in a lumen within the patient;
    deploying a first marker at a first location proximate a treatment target within the patient, wherein deploying the first marker includes
       moving a push wire of the catheter toward a distal end of the catheter or fixing the push wire in place and retracting the catheter toward a proximal end of the push wire, and
       releasing an anti-migration device of the first marker from the catheter such that the anti-migration device anchors the first marker at the first location, the anti-migration device having a shell assembly, an anchor sleeve, a fastener, and an anchor disk;
    deploying a second marker at a second location proximate the treatment target within the patient;
    tracking at least one of position, rotation, and motion of the treatment target, wherein the tracking includes:
       collecting at least one of position, rotation, and motion data of the first and second markers during radiation treatment, and
       calculating, in real time, at least one of position, rotation, and motion of the first and second markers using the at least one of the position, rotation, and motion data of the first and second markers;
    interrupting the radiation treatment when the at least one of the position, rotation, and motion of the first and second markers exceeds a predetermined offset value;
    realigning the patient to bring the at least one of the position, rotation, and motion of the first and second markers below the predetermined offset value before continuing the radiation treatment;
    determining whether to adapt the radiation plan based on at least one of changes in the treatment target and results of the radiation plan.

12. The method of claim 11, further comprising:
    imaging the first marker, the second marker, and the treatment target; and
    determining the relative distances between the markers and the relative distances between the markers and the treatment target.

13. The method of claim 11 wherein the first and the second markers are magnetic transponder markers having a circuit configured to be energized by a wirelessly transmitted pulsed magnetic field and to wirelessly transmit a pulsed magnetic location signal in response to the pulsed magnetic field.

14. The method of claim 11, further comprising spring-loading the first marker in the catheter.

15. The method of claim 11 wherein deploying the second marker at the second location proximate the treatment target includes repositioning the catheter to the second location.

16. The method of claim 11 wherein the catheter is a first catheter, and wherein deploying the second marker at the second location proximate the treatment target includes positioning a second catheter to the second location.

17. The method of claim 11 wherein the catheter includes at least one of a perforation, a crease, and a thinned section, and wherein deploying the first marker further includes applying a deployment force that exceeds a breakaway force of the at least one of the perforation, crease, and thinned section of the catheter such that the first marker breaks away and detaches from the catheter.

18. The method of claim 11 wherein the push wire has an integral retention device contained in the catheter, and wherein the method further comprises moving the push wire toward the distal end of the catheter to engage the marker.

19. The method of claim 18 wherein:

the method further comprises spring-loading the fasteners of the first marker in the catheter; and deploying the first marker includes releasing the first marker from the integral retention device of the push wire such that the fasteners of the first marker extends radially outward fixing the first marker at the first location.

20. The method of claim 19, further comprising engaging a first end portion of the first marker with the integral retention device of the push wire, wherein the first end portion of the first marker is spaced apart from the distal end of the catheter in a proximal direction.

* * * * *